US011638746B2

(12) United States Patent
Zhou

(10) Patent No.: US 11,638,746 B2
(45) Date of Patent: *May 2, 2023

(54) EXTENDED RELEASE OF NEUREGULIN FOR IMPROVED CARDIAC FUNCTION

(71) Applicant: Zensun (Shanghai) Science & Technology, Co., Ltd., Shanghai (CN)

(72) Inventor: Mingdong Zhou, Shanghai (CN)

(73) Assignee: Zensun (Shanghai) Science & Technology, Co., Ltd., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/965,790

(22) Filed: Dec. 10, 2015

(65) Prior Publication Data

US 2016/0095903 A1 Apr. 7, 2016

Related U.S. Application Data

(62) Division of application No. 11/648,061, filed on Dec. 29, 2006, now abandoned.

(60) Provisional application No. 60/758,626, filed on Jan. 13, 2006, provisional application No. 60/755,124, filed on Dec. 30, 2005.

(51) Int. Cl.
*A61K 38/18* (2006.01)
*A61K 9/00* (2006.01)
*A61K 9/127* (2006.01)
*A61K 48/00* (2006.01)
*A61K 47/60* (2017.01)

(52) U.S. Cl.
CPC ........ *A61K 38/1883* (2013.01); *A61K 9/0019* (2013.01); *A61K 47/60* (2017.08); *A61K 48/00* (2013.01); *A61K 9/127* (2013.01)

(58) Field of Classification Search
CPC ............... C07K 14/4756; C07K 14/00; A61K 38/1883; A61K 38/16; A61K 9/0019; A61K 9/0004; A61K 2039/54; A61K 2039/545; A61K 9/127; A61K 9/7023; A61M 5/142; A61M 5/14276
See application file for complete search history.

(56) References Cited

U.S. PATENT DOCUMENTS

| | | |
|---|---|---|
| 3,536,809 A | 10/1970 | Applezweig |
| 3,598,123 A | 8/1971 | Zaffaroni et al. |
| 3,773,919 A | 11/1973 | Boswell et al. |
| 3,845,770 A | 11/1974 | Theeuwes et al. |
| 3,916,899 A | 11/1975 | Theeuwes et al. |
| 4,002,531 A | 1/1977 | Royer |
| 4,008,719 A | 2/1977 | Theeuwes et al. |
| 4,088,864 A | 5/1978 | Theeuwes et al. |
| 4,179,337 A | 12/1979 | Davis et al. |
| 4,301,144 A | 11/1981 | Iwashita et al. |
| 4,485,045 A | 11/1984 | Regen |
| 4,496,689 A | 1/1985 | Mitra |
| 4,542,025 A | 9/1985 | Tice et al. |
| 4,544,545 A | 10/1985 | Ryan et al. |
| 4,640,835 A | 2/1987 | Shimizu et al. |
| 4,670,417 A | 6/1987 | Iwasaki et al. |
| 4,684,479 A | 8/1987 | D'Arrigo |
| 4,791,192 A | 12/1988 | Nakagawa et al. |
| 4,885,172 A | 12/1989 | Bally et al. |
| 4,897,268 A | 1/1990 | Tice et al. |
| 4,904,584 A | 2/1990 | Shaw |
| 5,059,421 A | 10/1991 | Loughrey et al. |
| 5,059,595 A | 10/1991 | Le Grazie |
| 5,073,543 A | 12/1991 | Marshall et al. |
| 5,120,548 A | 6/1992 | McClelland et al. |
| 5,171,578 A | 12/1992 | Bally et al. |
| 5,215,680 A | 6/1993 | D'Arrigo |
| 5,354,556 A | 10/1994 | Sparks et al. |
| 5,367,060 A | 11/1994 | Vandlen et al. |
| 5,399,331 A | 3/1995 | Loughrey et al. |
| 5,407,609 A | 4/1995 | Tice et al. |
| 5,530,109 A | 6/1996 | Goodearl et al. |
| 5,554,730 A | 9/1996 | Woiszwillo et al. |
| 5,573,776 A | 11/1996 | Harrison et al. |
| 5,578,709 A | 11/1996 | Woiszwillo |
| 5,586,110 A | 12/1996 | Nakaki et al. |
| 5,591,767 A | 1/1997 | Mohr et al. |
| 5,639,476 A | 6/1997 | Oshlack et al. |
| 5,639,480 A | 6/1997 | Bodmer et al. |
| 5,641,869 A | 6/1997 | Vandlen et al. |
| 5,667,780 A | 9/1997 | Ho et al. |
| 5,674,533 A | 10/1997 | Santus et al. |
| 5,714,385 A | 2/1998 | Mather et al. |

(Continued)

FOREIGN PATENT DOCUMENTS

| | | |
|---|---|---|
| AU | 68278/94 A | 12/1994 |
| CN | 1276381 A | 12/2000 |

(Continued)

OTHER PUBLICATIONS

Reddy KR. Controlled-release, pegylation, liposomal formulations: New mechanisms in the delivery of injectable drugs. Ann. Pharmacother. 2000, 34:915-923.*
"38th edition Gray's Anatomy. The anatomical basis of medicine and surgery," 1995, Churchill Livingstone, p. 770.
Balligand, et al., "Cardiac endothelium and tissue growth," *Prog Cardiovasc Dis.* Jan.-Feb. 1997; 39(4):351-360.
Bremer et al., "Protein delivery with infusion pumps," *Pharmaceutical Biotechnology,* 10:239-254 (1997).
Buchwald et al., "Inplatable pumps: Recent progress and anticipated future advances," *ASAIO J.,* 38(4):772-778 (1992).
Busfield et al., "Characterization of a neuregulin-related gene, Don-1, that is highly expressed in restricted regions of the cerebellum and hippocampus," *Mol. Cell Biol.,* 17(7):4007-4014 (1997).

(Continued)

*Primary Examiner* — Kimberly Ballard
(74) *Attorney, Agent, or Firm* — Jones Day

(57) ABSTRACT

The present invention provides extended release compositions comprising neuregulin for preventing, treating or delaying various diseases or disorders. The present invention also provides methods for preventing, treating or delaying various diseases or disorders by extended release of neuregulin.

10 Claims, 3 Drawing Sheets

Specification includes a Sequence Listing.

(56) References Cited

U.S. PATENT DOCUMENTS

| | | |
|---|---|---|
| 5,716,930 A | 2/1998 | Goodearl et al. |
| 5,721,139 A | 2/1998 | Mather et al. |
| 5,733,566 A | 3/1998 | Lewis |
| 5,739,108 A | 4/1998 | Mitchell |
| 5,824,784 A | 10/1998 | Kinstler et al. |
| 5,834,229 A | 11/1998 | Vandlen et al. |
| 5,840,525 A | 11/1998 | Vandlen et al. |
| 5,859,206 A | 1/1999 | Vandlen et al. |
| 5,874,104 A | 2/1999 | Adler-Moore et al. |
| 5,891,474 A | 4/1999 | Busetti et al. |
| 5,900,461 A | 5/1999 | Harris |
| 5,916,588 A | 6/1999 | Popescu et al. |
| 5,922,356 A | 7/1999 | Koseki et al. |
| 5,932,462 A | 8/1999 | Harris et al. |
| 5,942,252 A | 8/1999 | Tice et al. |
| 5,965,156 A | 10/1999 | Proffitt et al. |
| 5,968,511 A | 10/1999 | Akita et al. |
| 5,972,891 A | 10/1999 | Kamei et al. |
| 5,980,945 A | 11/1999 | Ruiz |
| 5,981,719 A | 11/1999 | Wioszwillo et al. |
| 5,993,855 A | 11/1999 | Yoshimoto et al. |
| 6,024,983 A | 2/2000 | Tice et al. |
| 6,033,660 A | 3/2000 | Mather et al. |
| 6,043,094 A | 3/2000 | Martin et al. |
| 6,045,830 A | 4/2000 | Igari et al. |
| 6,056,973 A | 5/2000 | Allen et al. |
| 6,087,323 A | 7/2000 | Gwynne et al. |
| 6,087,324 A | 7/2000 | Igari et al. |
| 6,090,925 A | 7/2000 | Woiszwillo et al. |
| 6,096,873 A | 8/2000 | Schaefer et al. |
| 6,110,498 A | 8/2000 | Rudnic et al. |
| 6,113,943 A | 9/2000 | Okada et al. |
| 6,121,415 A | 9/2000 | Godowski et al. |
| 6,126,966 A | 10/2000 | Abra et al. |
| 6,136,558 A | 12/2000 | Ballinger et al. |
| 6,156,728 A | 12/2000 | Gao et al. |
| 6,162,641 A | 12/2000 | Goldman et al. |
| 6,169,070 B1 | 1/2001 | Chen et al. |
| 6,197,350 B1 | 3/2001 | Yamagata et al. |
| 6,248,363 B1 | 6/2001 | Patel et al. |
| 6,252,051 B1 | 6/2001 | Godowski et al. |
| 6,264,970 B1 | 7/2001 | Hata et al. |
| 6,267,981 B1 | 7/2001 | Okamoto et al. |
| 6,268,053 B1 | 7/2001 | Woiszwillo et al. |
| 6,284,276 B1 | 9/2001 | Rudnic et al. |
| 6,294,191 B1 | 9/2001 | Meers et al. |
| 6,294,201 B1 | 9/2001 | Kettelhoit et al. |
| 6,303,148 B1 | 10/2001 | Hennink et al. |
| 6,316,024 B1 | 11/2001 | Allen et al. |
| 6,352,716 B1 | 3/2002 | Janoff et al. |
| 6,352,721 B1 | 3/2002 | Faour |
| 6,361,796 B1 | 3/2002 | Rudnic et al. |
| 6,376,461 B1 | 4/2002 | Igari et al. |
| 6,387,638 B1 | 5/2002 | Ballinger et al. |
| 6,395,302 B1 | 5/2002 | Hennink et al. |
| 6,399,746 B1 | 6/2002 | Vandlen et al. |
| 6,406,713 B1 | 6/2002 | Janoff et al. |
| 6,419,961 B1 | 7/2002 | Igari et al. |
| 6,436,386 B1 | 8/2002 | Roberts et al. |
| 6,444,642 B1 | 9/2002 | Skylar et al. |
| 6,446,242 B1 | 9/2002 | Lien et al. |
| 6,458,387 B1 | 10/2002 | Scott et al. |
| 6,514,532 B2 | 2/2003 | Rudnic et al. |
| 6,517,859 B1 | 2/2003 | Tice et al. |
| 6,534,090 B2 | 3/2003 | Puthli et al. |
| 6,589,548 B1 | 7/2003 | Oh et al. |
| 6,593,290 B1 | 7/2003 | Gao et al. |
| 6,613,358 B2 | 9/2003 | Randolph et al. |
| 6,635,249 B1 | 10/2003 | Marchionni et al. |
| 6,669,961 B2 | 12/2003 | Kim et al. |
| 6,699,500 B2 | 3/2004 | Okada et al. |
| 6,713,086 B2 | 3/2004 | Qiu et al. |
| 6,740,634 B1 | 5/2004 | Saikawa et al. |
| 6,750,196 B1 | 6/2004 | Reh et al. |
| 6,759,057 B1 | 7/2004 | Weiner et al. |
| 6,814,979 B2 | 11/2004 | Rudnic et al. |
| 6,838,076 B2 | 1/2005 | Patton et al. |
| 6,838,093 B2 | 1/2005 | Flanner et al. |
| 6,866,866 B1 | 3/2005 | Chen et al. |
| 6,890,918 B2 | 5/2005 | Burnside et al. |
| 7,037,888 B1 | 5/2006 | Sklar et al. |
| 7,087,246 B2 | 8/2006 | Kim et al. |
| 7,226,907 B1 | 6/2007 | Zhou |
| 7,612,164 B2 | 11/2009 | Zhou |
| 8,609,620 B2 | 12/2013 | Zhou |
| 8,785,387 B2 | 7/2014 | Zhou |
| 9,434,777 B2 | 9/2016 | Zhou |
| 9,555,076 B2 | 1/2017 | Zhou |
| 9,580,515 B2 | 2/2017 | Zhou |
| 9,655,949 B2 | 5/2017 | Zhou |
| 2006/0019888 A1 | 1/2006 | Zhou |
| 2006/0194734 A1 | 8/2006 | Zhou |
| 2006/0199767 A1 | 9/2006 | Zhou |
| 2007/0129296 A1 | 6/2007 | Zhou |
| 2007/0190127 A1 | 8/2007 | Zhou |
| 2007/0213264 A1 | 9/2007 | Zhou |
| 2007/0264254 A1 | 11/2007 | Zhou |
| 2009/0156488 A1 | 6/2009 | Zhou |
| 2009/0203595 A1 | 8/2009 | Zhou |
| 2011/0229444 A1 | 9/2011 | Zhou |
| 2013/0078235 A1 | 3/2013 | Zhou |
| 2013/0079281 A1 | 3/2013 | Zhou |
| 2014/0031284 A1 | 1/2014 | Zhou |
| 2014/0135265 A1 | 5/2014 | Zhou |
| 2014/0364366 A1 | 12/2014 | Zhou |
| 2016/0089329 A1 | 3/2016 | Zhou |
| 2016/0095903 A1 | 4/2016 | Zhou |
| 2016/0297859 A1 | 10/2016 | Zhou |
| 2017/0007671 A1 | 1/2017 | Zhou |
| 2017/0189489 A1 | 7/2017 | Zhou |
| 2017/0232068 A1 | 8/2017 | Zhou |
| 2017/0313784 A1 | 11/2017 | Zhou |
| 2017/0360889 A1 | 12/2017 | Zhou |
| 2017/0368140 A1 | 12/2017 | Zhou |
| 2018/0104311 A1 | 4/2018 | Zhou |

FOREIGN PATENT DOCUMENTS

| | | |
|---|---|---|
| CN | 1138785 C | 2/2004 |
| CN | 1498656 A | 5/2004 |
| DE | 3218121 A1 | 11/1983 |
| EP | 0 036 676 A1 | 9/1981 |
| EP | 0 052 322 A2 | 5/1982 |
| EP | 0 058 481 A1 | 8/1982 |
| EP | 0 088 046 A2 | 9/1983 |
| EP | 0 102 324 A2 | 3/1984 |
| EP | 0 143 949 A1 | 6/1985 |
| EP | 0 133 988 A2 | 3/1995 |
| EP | 0 647 449 A1 | 4/1995 |
| EP | 0 142 641 A2 | 5/1995 |
| JP | 60007934 A | 1/1985 |
| JP | S607934 A | 1/1985 |
| WO | WO 89/01489 | 2/1989 |
| WO | WO 92/18627 | 10/1992 |
| WO | WO 94/00140 | 1/1994 |
| WO | WO 94/26298 | 11/1994 |
| WO | WO 95/32724 | 12/1995 |
| WO | WO 96/15812 | 5/1996 |
| WO | WO 97/09425 | 3/1997 |
| WO | WO 99/18976 | 4/1999 |
| WO | WO 00/37095 | 6/2000 |
| WO | WO 00/64400 | 11/2000 |
| WO | WO 01/89568 A1 | 11/2001 |
| WO | WO 03/080835 A1 | 10/2003 |
| WO | WO 03/099300 | 12/2003 |
| WO | WO 03/099320 | 12/2003 |
| WO | WO 03/099321 | 12/2003 |
| WO | WO 2007/062594 A1 | 6/2007 |
| WO | WO 2007/076701 A1 | 7/2007 |
| WO | WO 2008/028405 A1 | 3/2008 |
| WO | WO 2009/033373 A1 | 3/2009 |
| WO | WO 2010/060265 A1 | 6/2010 |
| WO | WO 2010/060266 A1 | 6/2010 |
| WO | WO 2010/142141 A1 | 12/2010 |

(56) References Cited

FOREIGN PATENT DOCUMENTS

| WO | WO 2011/091723 A1 | 8/2011 |
|---|---|---|
| WO | WO 2013/053076 A1 | 4/2013 |
| WO | WO 2013/053158 A1 | 4/2013 |
| WO | WO 2013/053201 A1 | 4/2013 |
| WO | WO 2014/187342 A1 | 11/2014 |
| WO | WO 2015/101182 A1 | 7/2015 |
| WO | WO2016/045493 A1 | 3/2016 |
| WO | WO2016/058493 A1 | 4/2016 |

OTHER PUBLICATIONS

Carraway et al., "Neuregulin-2, a new ligand of ErbB3/ErbB4-receptor tyrosine kinases," Nature, 387(6632):512-516(1997).
Chang H et al., "Ligands for ErbB-family receptors encoded by a neuregulin-like gene," Nature. May 29, 1997;387(6632):509-512.
Chien KR, "Molecular advances in cardiovascular biology," Science. May 14, 1993;260(5110):916-917.
Chien, et al., "Regulation of cardiac gene expression during myocardial growth and hypertrophy: molecular studies of an adaptive physiologic response," FASEB J. Dec. 1991; 5(15):3037-3046.
Colucci, et al., "Pathphysiology of heart failure," Chapter 13 in Heart Diseases: A textbook of cardiovascular medicine, Braunwald, ed., Saunders, Philadelphia. 1996; 5:394-420.
Crone SA, "ErbB2 is essential in the prevention of dilated cardiomyopathy," Nat Med. May 2002;8(5):459-465.
Dias, et al., "The molecular basis of skeletal muscle differentiation," Semin Diagn Pathol. Feb. 1994; 11(1):3-14.
Eppstein, et al., "Biological activity of liposome-encapsulated murine interferon gamma is mediated by a cell membrane receptor," Proc Natl Acad Sci U S A. Jun. 1985; 82(11):3688-3692.
Falls et al., "ARIA, a protein that stimulates acetylcholine receptor synthesis, is a member of the neu ligand family," Cell, 72(5):801-815 (1993).
Florini-Jr., et al., "Stimulation of myogenic differentiation by a neuregulin, glial growth factor 2," J Biol Chem, May 31, 1996; 271(22):12699-12702.
Gray H., Gray's Anatomy: The Anatomical Basis of Medicine and Surgery, 1995, Ed. Williams et al., Churchill Livingstone, Edinburgh, pp. 264-254, 298-310 and 739-771.
Harari et al., "Neuregulin-4: a novel growth factor that acts through the ErbB-4 receptor tyrosine kinase," Oncogene, 18(17):2681-2689 (1999).
Higashiyama et al., "A novel brain-derived member of the epidermal growth factor family that interacts with ErbB3 and ErbB4," J. Biochem., 122(3):675-680 (1997).
Hijazi et al., "NRG-3 in human breast cancers: activation of multiple erbB family proteins," Int. J. Oncol., 13:1061-1067 (1998).
Holmes, et al., "Identification of heregulin, a specific activator of p185erbB2," Science. May 22, 1992; 256(5060):1205-1210.
Hwang, et al., "Hepatic uptake and degradation of unilamellar sphingomyelin/cholesterol liposomes: a kinetic study," Proc Natl Acad Sci U S A. Jul. 1980; 77(7):4030-4034.
International Search Report from International Application No. PCT/CN2006/003694, dated Apr. 12, 2007.
Izumo S, "Calcineurin—the missing link in cardiac hypertrophy," Nat Med. Jun. 1998;4(6):661-662.
Kuramochi et al., "Myocyte contractile activity modulatese norepinephrine cytotoxicity and survival effects of neuregulin-1β," Am. J. Physiol. Cell Physiol., 286:C222-C229 (2004).
Langer, "Controlled release of macromoleucles," Chemtech, 12:98-105—(1982).
Langer, et al., "Biocompatibility of polymeric delivery systems for macromolecules," J Biomed Mater Res. Mar. 1981; 15(2):267-277.
Lemke, "Neuregulins in development," Mol. Cell Neurosci., 7(4):247-262 (1996).
Marchionni et al., "Glial growth factors are alternatively spliced erbB2 ligands expressed in the nervous system," Nature, 362(6418):312-318 (1993).

Olson, "Regulation of muscle transcription by the MyoD family. The heart of the matter," Circ Res. Jan. 1993; 72(1):1-6.
Parker, et al., "p53-independent expression of p21Cipl in muscle and other terminally differentiating cells," Science. Feb. 17, 1995; 267(5200):1024-1027.
Peles and Yarden, "Neu and its ligands: from an oncogene to neural factors," Bioessays, 15(12):815-824 (1993).
Peles et al., "Isolation of the neu/HER-2 stimulatory ligand: a 44 kd glycoprotein that induces differentiation of mammary tumor cells," Cell, 69(1):205-216 (1992).
Perkins et al., "The use of mini-osmotic pumps in continuous infusion studies," Chapter 21 of Handbook of pre-clinical continues intravenous infusion. Healing G., Smith D., editors, Taylor and Francis, London, pp. 265-281 (2000).
Physicians' Desk Reference. Medical Economics Data Production Co., Montvale, NJ. 1994; pp. 2314-2320.
Rumyantsev, "Interrelations of the proliferation and differentiation processes during cardiac myogenesis and regeneration," Int Rev Cytol. 1977; 51:186-273.
Sadick et al., "Analysis of heregulin-induced ErbB2 phosphorylation with a high-throughput Kinase receptor activation enzyme-linked immunosorbant assay," Anal. Biochem., 235(2):207-214 (1996).
Sidman, et al., "Controlled release of macromolecules and pharmaceuticals from synthetic polypeptides based on glutamic acid," Biopolymers. Jan. 1983; 22(1):547-556.
Simpson, et al., "Myocyte hypertrophy in neonatal rat heart cultures and its regulation by serum and by catecholamines," Circ Res. Dec. 1982; 51(6):787-801.
Sindone et al., "Continuous home ambulatory intravenous inotropic drug therapy in severe heart failure: safety and cost efficacy," American Heart J., 134(5):889-999 (1997).
Stevenson et al., "Optimizing therapy for complex or refractory heart failure: a management algorithm," Am Heart J. Jun. 1998;135(6 Pt 2 Su):S293-S309.
Swynghedauw B, "Molecular mechanisms of myocardial remodeling," Physiol Rev. Jan. 1999;79(1):215-262.
Urquhart et al., "Rate-controlled delivery systems in drug and hormone research," Ann. Rev. Pharmacol. Toxicol., 24:199-236 (1984).
Van Meyel et al., "Continuous infusion of furosemide in the treatment of patients with congestive heart failure and diuretic resistance," J. Internal Med., 235:329-334 (1994).
Verma et al., "Osmotic pumps in drug delivery," Crit. Rev. Therapeutic Drug Carrier Systems, 21(6):477-520 (2004).
Wen et al., "Neu differentiation factor: a transmembrane glycoprotein containing an EGF domain and an immunoglobulin homology unit," Cell, 69(3):559-572 (1992).
Xu et al., "Neuregulin-1/ErbB signaling: a druggable target for treating heart failure," Curr. Opin. Pharmacol., 9(2):214-219 (2009).
Zhao, et al., "Neuregulins promote survival and growth of cardiac myocytes. Persistence of ErbB2 and ErbB4 expression in neonatal and adult ventricular myocytes," J Biol Chem. Apr. 24, 1998; 273(17):10261-10269.
Zhao, et al., "Selective disruption of neuregulin-1 function invertebrate embryos using ribozyme-tRNA transgenes," Development. May 1998; 125(10):1899-1907.
Zhou, et al., "Retinoid-dependent pathways suppress myocardial cell hypertrophy," Proc Natl Acad Sci U S A. Aug. 1, 1995; 92(16):7391-7395.
Stevenson et al., "Osmotic implantable delivery systems," Handbook of Pharmaceutical Controlled Release Technology, Wise DL editor, 225-226 (2000).
Burke, "Controlled release protein therapeutics: effects of process and formulation on stability," Handbook of Pharmaceutical Controlled Release Technology, Wise DL editor, 661-663 (2000).
Lollini et al., "Vaccines for tumour prevention," Nat. Rev. Cancer, 6(3):204-216 (2006).
Vickers, "A vaccine against alzheimer's disease," Drugs Aging, 19(7):487-494 (2002).
Xu et al.., "Neuroprotection by neuregulin-1 following focal stroke is associated with the attenuation of ischemia-induced pro-inflammatory and stree gene exrpession," Neurobiology Dis., 19:461-470 (2005).

(56) References Cited

OTHER PUBLICATIONS

Krag et al., "Heregulin ameliorates the dystrophic phenotype in mdx mice," *Proc. Natl. Acad. Sci.*, USA, 101(38):13856-13860 (2004).
Penderis et al., "Increasing local levels of neuregulin (glial growth factor-2) by direct infusion into areas of demyelination does not alter remyelination in the rat CNS," *Eur. J. Neurosci.*, 18:2253-2264 (2003).

* cited by examiner

EXTENDED RELEASE OF NEUREGULIN FOR IMPROVED CARDIAC FUNCTION

CROSS REFERENCE TO RELATED APPLICATIONS

This application is a divisional of U.S. Ser. No. 11/648,061, filed Dec. 29, 2006, which claims the benefit of priority of U.S. provisional application Nos. 60/755,124, filed Dec. 30, 2005, and 60/758,626, filed Jan. 13, 2006.

SEQUENCE LISTING

This application incorporates by reference in its entirety the Computer Readable Form (CRF) of a Substitute Sequence Listing in ASCII text format submitted via EFS-Web. The Substitute Sequence Listing text file submitted via EFS-Web is entitled "11748-038-999_SUB_SEQ_LISTING.txt," was created on Sep. 14, 2022, and is 1,658 bytes in size.

FIELD OF THE INVENTION

This invention relates generally to compositions and methods for preventing, treating or delaying various cardiac diseases or disorders by extended release of neuregulin to a mammal.

BACKGROUND OF THE INVENTION

Cardiac (ventricular) hypertrophy is an important adaptive physiological response to increased stress or demands for cardiac work. One of the early cellular changes that occurs after a stimulus for hypertrophy is the synthesis of mitochondria and expansion of myofibrillar mass (wall thickening) with a proportional increase in the size of individual cells, but no (or minimal) increase in the number of cells.

When the ventricle is stressed, the initial response is an increase in sarcomere length. This is followed by an increase in the total muscle mass. When the overload is severe; myocardial contractility becomes depressed. In its mildest form, this depression is manifested by a reduction in the velocity of shortening of unloaded myocardium or by a reduction in the rate of force development during isometric contraction. As myocardial contractility becomes further depressed, a more extensive reduction in the velocity of shortening of unloaded myocardium occurs, now accompanied by a decline in isometric force development and shortening. At this point, circulatory compensation may still be provided by cardiac dilation and an increase in muscle mass, which tend to maintain wall stress at normal levels. As contractility falls further, overt congestive heart failure, reflected in a depression of cardiac output and work and/or an elevation of ventricular end-diastolic volume and pressure at rest, supervenes.

The transition from hypertrophy to heart failure is characterized by several alterations in cellular organization. For example, normal hypertrophic cells have a large size with increased and well organized contractile units, as well as strong cell-cell adhesions. In contrast, pathologically hypertrophic cells, which also have large size and accumulation of proteins, display disorganization of contractile proteins (disarray of sarcomeric structures) and poor cell-cell adhesions (disarray of myofibers). Thus, in pathological hypertrophy, the increased size and accumulation of contractile proteins are associated with disorganized assembly of sarcomeric structures and a lack of robust cell-cell interactions.

Heart failure affects approximately five million Americans, and more than 550,000 new patients are diagnosed with the condition each year. Current drug therapy for heart failure is primarily directed to angiotensin-converting enzyme (ACE) inhibitors, which are vasodilators that cause blood vessels to expand, lowering blood pressure and reducing the heart's workload. While the percent reduction in mortality has been significant, the actual reduction in mortality with ACE inhibitors has averaged only 3%-4%, and there are several potential side effects.

ACE inhibitors have also been administered in combination with other drugs such as digitalis, which increases the force of the heart's contractions, and/or a diuretic, which helps relieve the heart's workload by causing the kidneys to remove more sodium and water from the bloodstream. However, at least one study demonstrated no difference in survival associated with the use of digitalis compared with placebo in patients with Class II-III heart failure. Additionally, diuretics can improve some symptoms of heart failure but it is not suitable as a sole treatment.

Additional limitations are associated with other options for preventing or treating heart failure. For example, heart transplantation is clearly more expensive and invasive than drug treatment, and it is further limited by the availability of donor hearts. Use of mechanical devices, such as biventricular pacemakers, are similarly invasive and expensive. Thus, there has been a need for new therapies given the deficiencies in current therapies.

One promising new therapy involves administration of neuregulin (hereinafter referred to as "NRG") to a patient suffering from or at risk of developing heart failure. NRGs comprise a family of structurally related growth and differentiation factors that include NRG1, NRG2, NRG3 and NRG4 and isoforms thereof. For example, over 15 distinct isoforms of NRG1 have been identified and divided into two large groups, known as α- and β-types, on the basis of differences in the sequence of their essential epidermal growth factor (EGF)-like domains.

NRGs bind to the EGF receptor family, which comprises EGFR, ErbB2, ErbB3 and ErbB4, each of which plays an important role in multiple cellular functions, including cell growth, differentiation and survival. They are protein tyrosine kinase receptors, consisting of an extracellular ligand-binding domain, transmembrane domain and cytoplasmic tyrosine kinase domain. After NRG binds to the extracellular domain of ErbB3 or ErbB4, it induces a conformational change that leads to heterodimer formation between ErbB3, ErbB4 and ErbB2 or homodimer formation between ErbB4 itself, which results in phosphorylation of the receptors' C-terminal domain inside the cell membrane. The phosphorylated intracellular domain then binds additional signal proteins inside the cell, activating the corresponding downstream AKT or ERK signaling pathway, and inducing a series of cell reactions, such as stimulation or depression of cell proliferation, cell differentiation, cell apoptosis, cell migration or cell adhesion. Among these receptors, mainly ErbB2 and ErbB4 are expressed in the heart.

It has been shown that the EGF-like domains of NRG1, ranging in size from 50 to 64-amino acids, are sufficient to bind to and activate these receptors. Previous studies have shown that neuregulin-1β (NRG-1β) can bind directly to ErbB3 and ErbB4 with high affinity. The orphan receptor, ErbB2, can form heterodimer with ErbB3 or ErbB4 with higher affinity than ErbB3 or ErbB4 homodimers. Research in neural development has indicated that the formation of the sympathetic nervous system requires an intact NRG-1β, ErbB2 and ErbB3 signaling system. Targeted disruption of the NRG-1β or ErbB2 or ErbB4 led to embryonic lethality due to cardiac development defects. Recent studies also highlighted the roles of NRG-1β, ErbB2 and ErbB4 in the cardiovascular development as well as in the maintenance of adult normal heart function. NRG-1β has been shown to enhance sarcomere organization in adult cardiomyocytes. The short-term administration of a recombinant NRG-1β EGF-like domain significantly improves or protects against deterioration in myocardial performance in three distinct animal models of heart failure. More importantly, NRG-1β significantly prolongs survival of heart failure animals. These effects make NRG-1β promising as a broad spectrum therapeutic or lead compound for heart failure due to a variety of common diseases. However, there is still a need for more effective methods of using NRG, which can be used in a clinical setting for the prevention, treatment or delaying of heart failure and/or cardiac hypertrophy.

SUMMARY OF THE INVENTION

Extended release of NRG greatly improves the effect of NRG in the treatment of heart failure and cardiac hypertrophy compared to NRG administered by other methods. Extended release of NRG also has the benefit of reducing the adverse side effects of NRG compared to NRG administered by other methods. Thus, the present invention relates to compositions and methods for preventing, treating or delaying various cardiac diseases or disorders in mammals, particularly in humans, by extending the release of a NRG protein, or a functional fragment thereof, or a nucleic acid encoding a NRG protein, or a functional fragment thereof, or an agent that enhances production and/or function of said NRG.

In a first aspect of the invention, a method is provided for preventing, treating or delaying heart failure in a mammal, the method comprising extended release of NRG into a mammal in need thereof.

In one embodiment of the method for preventing, treating or delaying heart failure in a mammal, the extended release of NRG into a mammal leads to sustained activation of the ERK signaling pathway in cardiac cells.

In another embodiment of the method for preventing, treating or delaying heart failure in a mammal in need thereof, the extended release of NRG into a mammal results in sustained activation of the AKT signaling pathway in cardiac cells.

In another embodiment of the method for preventing, treating or delaying heart failure in a mammal in need thereof, the extended release of NRG into a mammal enhances the EF and/or FS values of the left ventricle of mammal. In some embodiments, the EF value of the mammal is enhanced by a percentage selected from the group consisting of greater than about 20%, greater than about 30%, greater than about 40%, greater than about 50% and greater than about 60%. In some embodiments, the FS value of the mammal is enhanced by a percentage selected from the group consisting of greater than about 20%, greater than about 30%, greater than about 40%, greater than about 50% and greater than about 60%.

In another embodiment of the method for preventing, treating or delaying heart failure in a mammal in need thereof, the extended release of NRG into a mammal prevents cardiac hypertrophy.

Any extended release technology known in the art, including, but not limited to, an osmotic pump or syringe pump, poly-ethylene glycol ("PEG") coupling, and/or liposome or microsphere packaging, can be used in the present invention.

In a second aspect of the invention, a method is provided for reducing the interior diameter of the left ventricle, the method comprising extended release of NRG into a mammal in need thereof. In one preferred embodiment, extended release of NRG into a mammal reduces the LVEDD value by greater than about 2%. More preferably, extended release of NRG into a mammal reduces the LVEDD value by greater than about 5%. Even more preferably, extended release of NRG into a mammal reduces the LVEDD value by greater than about 10%. More preferably, extended release of NRG into a mammal reduces the LVEDD value by greater than about 15%. Most preferably, extended release of NRG into a mammal reduces the LVEDD value by greater than about 20%.

In another preferred embodiment, extended release of NRG into a mammal reduces the LVESD value by greater than about 2%. More preferably, extended release of NRG into a mammal reduces the LVESD value by greater than about 5%. Even more preferably, extended release of NRG into a mammal reduces the LVESD value by greater than about 10%. Even more preferably, extended release of NRG into a mammal reduces the LVESD value by greater than about 15%. Most preferably, extended release of NRG into a mammal decreases the LVESD value by greater than about 20%.

In a third aspect of the invention, a method is provided for causing cardiomyocyte growth and/or differentiation, the method comprising extended release of NRG into a mammal in need thereof thereby activating the MAP kinase pathway in cardiac cells and causing growth and/or differentiation of the cardiomyocyte.

In a fourth aspect of the invention, a method is provided for inducing remodeling of muscle cell sarcomeric and cytoskeleton structures, or cell-cell adhesions, the method comprising extended release of NRG into a mammal in need thereof thereby activating the MAP kinase pathway in cardiac cells and causing remodeling of the cell structures or the cell-cell adhesions.

In a fifth aspect of the invention, a method is provided for treating or preventing disassociation of cardiac muscle cell-cell adhesion and/or the disarray of sarcomeric structures in a mammal in need thereof, the method comprising extended release of NRG into a mammal.

Additionally, because NRG's interaction with ErbB receptors has been implicated in other diseases and disorders, extended release of NRG may also greatly improve the effect of NRG in the treatment of such other diseases and disorders compared to NRG administered by other methods. Thus, the present invention also relates to compositions and methods for preventing, treating or delaying various diseases or disorders in mammals, particularly in humans, by extending the release of a NRG protein, or a functional fragment thereof, or a nucleic acid encoding a NRG protein, or a functional fragment thereof, or an agent that enhances production and/or function of said NRG. Such diseases and disorders include generally those of the central and peripheral nervous system. Examples of other diseases and disorders, include, various cardiovascular diseases, cancer, neural system disease and/or muscle diseases, including muscular dystrophy (e.g., Duchenne, Limb-girdle) and multiple sclerosis, spinal injury, eye and ear diseases, diabetes, schizophrenia, and Alzheimer's.

The invention also provides an extended release composition or formulation of NRG for preventing, treating or delaying heart failure in a mammal. In one embodiment, the composition or formulation sustains activation of the ERK signaling pathway in cardiac cells. In another embodiment, the composition or formulation sustains activation of the AKT signaling pathway in cardiac cells. In another embodiment, the composition or formulation enhances the EF and/or FS values of the mammal. In yet another embodiment, the composition or formulation prevents cardiac hypertrophy. The composition or formulation may incorporate the use of any extended release technology known in the art, including, but not limited to, an osmotic pump or syringe pump, poly-ethylene glycol (PEG) coupling, and/or liposome or microsphere packaging.

The invention also provides a kit comprising a NRG composition or formulation and an extended release technology known in the art, including, but not limited to, an osmotic pump or syringe pump, poly-ethylene glycol (PEG) coupling, and/or liposome or microsphere packaging. In some embodiments, the kit further comprises an instruction for using the NRG composition or formulation and or extended release technology in preventing, treating or delaying heart failure in a mammal; preventing, treating or delaying cardiac hypertrophy in a mammal; or reducing the interior diameter of the left ventricle in a mammal.

Those and other aspects, objects, advantages and features of the invention will be apparent to those persons skilled in the art upon reading the disclosure of the invention as more fully described below.

DETAILED DESCRIPTION OF THE INVENTION

Figure 1:
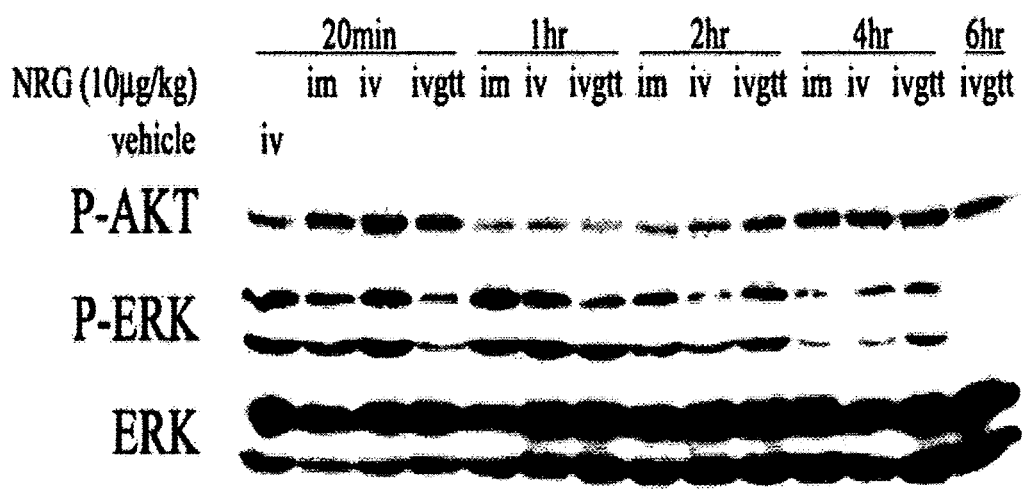
FIG. 1 shows the phosphorylation of AKT and ERK in the left ventricle of rats over time after NRG was infused by intramuscular injection, intravenous injection and intravenous glucose tolerance test infusion. "P-AKT," "P-ERK" and "NRG" mean phosphorylated AKT, phosphorylated ERK and neuregulin. "im," "iv," and "ivgtt" mean intramuscular injection, intravenous injection and intravenous glucose tolerance test, respectively.

Although any methods similar or equivalent to those described herein can be used in the practice of the present invention, the preferred methods and materials are now described.

The present invention provides methods for treating or preventing heart failure or cardiac hypertrophy in a mammal by extended release of a sustained or varied amount of NRG. Preferably, the mammal is a human patient suffering from or at risk of developing heart failure.

For clarity of disclosure, and not by way of limitation, the detailed description of the invention hereinafter is divided into the subsections that follow. All publications mentioned herein are incorporated by reference to disclose and describe the methods and/or materials in connection with which the publications are cited.

A. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, the singular forms "a", "an", and "the" mean "at least one" or "one or more" unless the context clearly dictates otherwise.

As used herein, "neuregulin" or "NRG" used in the present invention refers to proteins or peptides that can bind and activate ErbB2, ErbB3, ErbB4 or combinations thereof, including but not limited to all neuregulin isoforms, neuregulin EGF domain alone, polypeptides comprising neuregulin EGF-like domain, neuregulin mutants or derivatives, and any kind of neuregulin-like gene products that also activate the above receptors as described in detail below. In preferred embodiments, neuregulin used in the present invention binds to and activates ErbB2/ErbB4 or ErbB2/ErbB3 heterodimers. Neuregulin also includes NRG-1, NRG-2, NRG-3, and NRG-4 proteins, peptides, fragments and compounds that mimic the activities of neuregulin. Neuregulin used in the present invention can activate the above ErbB receptors and modulate their biological reactions, e.g., stimulate breast cancer cell differentiation and milk protein secretion; induce the differentiation of neural crest cell into Schwann cell; stimulate acetylcholine receptor synthesis in skeletal muscle cell; and/or improve cardiocyte differntiation, survival and DNA synthesis. Neuregulin also includes those variants with conservative amino acid substitutions that do not substantially alter their biological activity. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al. Molecular Biology of the Gene, 4th Edition, 1987, The Bejacmin/Cummings Pub. co., p. 224).

Neuregulin protein encompasses neuregulin protein and peptide. Neuregulin nucleic acid encompasses neuregulin nucleic acid and neuregulin oligonucleotide.

As used herein, "epidermal growth factor-like domain" or "EGF-like domain" refers to a polypeptide motif encoded by the neuregulin gene that binds to and activates ErbB2, ErbB3, ErbB4, or combinations thereof, and bears a structural similarity to the EGF receptor-binding domain as disclosed in WO 00/64400, Holmes et al., Science, 256: 1205-1210 (1992); U.S. Pat. Nos. 5,530,109 and 5,716,930; Hijazi et al., Int. J. Oncol., 13:1061-1067 (1998); Chang et al., Nature, 387:509-512 (1997); Carraway et al., Nature, 387:512-516 (1997); Higashiyama et al., J. Biochem., 122: 675-680 (1997); and WO 97/09425, the contents of which are all incorporated herein by reference. In certain embodiments, EGF-like domain binds to and activates ErbB2/ErbB4 or ErbB2/ErbB3 heterodimers. In certain embodiments, EGF-like domain comprises the amino acid sequence of the receptor binding domain of NRG-1. In some embodiments, EGF-like domain comprises the amino acid sequence corresponding to amino acid residues 177-226, 177-237, or 177-240 of NRG-1. In certain embodiments, EGF-like domain comprises the amino acid sequence of the receptor binding domain of NRG-2. In certain embodiments, EGF-like domain comprises the amino acid sequence of the receptor binding domain of NRG-3. In certain embodiments, EGF-like domain comprises the amino acid sequence of the receptor binding domain of NRG-4. In certain embodiments, EGF-like domain comprises the amino acid sequence of Ala Glu Lys Glu Lys Thr Phe Cys Val Asn Gly Gly Glu Cys Phe Met Val Lys Asp Leu Ser Asn Pro (SEQ ID NO:3), as described in U.S. Pat. No. 5,834,229.

As used herein, an "effective amount" of an active agent for treating a particular disease is an amount that is sufficient to ameliorate, or in some manner reduce the symptoms associated with the disease. The amount may cure the disease but, typically, is administered in order to ameliorate the symptoms of the disease.

As used herein, "active agent" means any substance intended for the diagnosis, cure, mitigation, treatment, or prevention of disease in humans and other animals, or to otherwise enhance physical and mental well being.

As used herein, "amelioration" of the symptoms of a particular disorder by administration of a particular active agent refers to any lessening, whether permanent or temporary, lasting or transient that can be attributed to or associated with administration of the agent.

As used herein, "treat", "treatment" and "treating" refer to any manner in which the symptoms of a condition, disorder or disease are ameliorated or otherwise beneficially altered. The effect may be prophylactic in terms of completely or partially preventing a disease or symptom thereof and/or may be therapeutic in terms of a partial or complete cure for a disease and/or adverse effect attributable to the disease. Treatment also encompasses any pharmaceutical use of the compositions herein.

As used herein, "vector (or plasmid)" refers to discrete elements that are used to introduce heterologous DNA into cells for either expression or replication thereof. Selection and use of such vehicles are well known within the skill of the artisan. An expression vector includes vectors capable of expressing DNA that are operatively linked with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

As used herein, "cardiac muscle cell differentiation" means a condition characterized by the decrease in DNA synthesis by more than 10%, inhibition of other factor-stimulated DNA synthesis more than 10%, well organized sarcomeric structures and cell-cell adhesions, sustained activation of MAP kinases, and enhanced expression of p21$^{CIP1}$. Further discussion is provided in WO00/37095, the contents of which are incorporated herein by reference in their entireties.

As used herein, "ejection fraction" or "EF" means the portion of blood that is pumped out of a filled ventricle as the result of a heartbeat. It may be defined by the following formula: (LV diastolic volume—LV systolic volume)/LV diastolic volume.

As used herein, "fractional shortening" or "FS" means a ratio of the change in the diameter of the left ventricle between the contracted and relaxed states. It may be defined by the following formula: (LV end diastolic diameter—LV end systolic diameter)/LV end diastolic diameter.

As used herein, "heart failure" means an abnormality of cardiac function where the heart does not pump blood at the rate needed for the requirements of metabolizing tissues. Heart failure includes a wide range of disease states such as congestive heart failure, myocardial infarction, tachyarrhythmia, familial hypertrophic cardiomyopathy, ischemic heart disease, idiopathic dilated cardiomyopathy, myocarditis and the like. The heart failure can be caused by any number of factors, including, without limitation, ischemic, congenital, rheumatic, or idiopathic forms. Chronic cardiac hypertrophy is a significantly diseased state which is a precursor to congestive heart failure and cardiac arrest.

As used herein, "myocardial infarction" refers to a blockade of a coronary artery or blood flow interruption leading to focal necrosis of part of the myocardium caused by severe and persistent ischemia. As used herein, "extended release" refer s to providing continuous therapeutic level of an active agent (e.g., neuregulin) over a period of time. The extended release includes, without limitation various forms of release, such as continuous release, controlled release, delayed release, depot, gradual release, long-term release, programmed release, prolonged release, proportionate release, protracted release, repository, retard, slow release, spaced release, sustained release, time coat, timed release, delayed action, extended action, layered-time action, long acting, prolonged action, repeated action, slow acting, sustained action, sustained-action medications, and controlled release. The ability to obtain extended release, controlled release, timed release, sustained release, delayed release, long acting, pulsatile delivery or immediate release is performed using well-known procedures and techniques available to the ordinarily skilled artisan.

The amount of time over which the active agent continues to be released depends on the characteristics of the active agent and the extended release technology or technologies used, but in all cases is longer than that of administration of the active agent without the extended release technology or technologies.

As used herein, "microsphere" is synonymous with "microparticle", "microcapsule", "nanosphere", "nanoparticle" and "nanocapsule" unless the context clearly dictates otherwise.

As used herein, "pegylate" means to attach at least one Poly (ethylene glycol) molecule or at least one derivative of Poly (ethylene glycol) to an active agent or other molecule.

As used herein, "organized, or enhanced organization of sarcomeres or sarcomeric structures" means a condition characterized by the straight array of contractile proteins revealed by immunofluorescent staining of α-actinin in cardiac muscle cells. The straight array of α-actinin proteins in cells can be distinguished by microscopy and its connected photography. As used herein, "disorganized or disarray of sarcomeres or sarcomeric structures" means the opposite of the "organized, or enhanced organization of sarcomeres or sarcomeric structures"

As used herein, "organized, or enhanced organization of cytoskeleton structures" means a condition characterized by the straight actin fibers revealed by phalloidin staining of cardiac muscle cells. The straight actin fibers in cells can be distinguished by microscopy and its connected photography as exampled in figures of this specification. As used herein, "disorganized or disarray of cytoskeleton structures" means the opposite of "organized, or enhanced organization of cytoskeleton structures".

As used herein, "protein" is synonymous with "polypeptide" or "peptide" unless the context clearly dictates otherwise.

As used herein, "sustained activation of MAP kinases" means that the phosphorylated state of MAP kinases, p42/44, is maintained for at least 21 hr in cells. Further discussion is provided in WO00/37095, the contents of which are incorporated herein by reference.

The terms "synergistic, "synergistic effect" and like are used herein to describe improved treatment effects obtained by combining one or more therapeutic agents with one or more retinoic acid compounds. Although a synergistic effect in some fields is meant an effect which is more than additive (e.g., 1+1=3), in the field of medical therapy an additive (1+1=2) or less than additive (1+1=1.6) effect may be synergistic. For example, if each of two drugs were to inhibit the development of ventricular muscle cell hypertrophy by 50% if given individually, it would not be expected that the two drugs would be combined to completely stop the development of ventricular muscle cell hypertrophy. In many instances, due to unacceptable side effects, the two drugs cannot be administered together. In other instances, the drugs counteract each other and slow the development of ventricular muscle cell hypertrophy by less than 50% when administered together. Thus, a synergistic effect is said to be obtained if the two drugs slow the development of ventricular muscle cell hypertrophy by more than 50% while not causing an unacceptable increase in adverse side effects.

As used herein "cardiac hypertrophy" means a condition characterized by an increase in the size of individual ventricular muscle cells, the increase in cell size being sufficient to result in a clinical diagnosis of the patient or sufficient as to allow the cells to be determined as larger (e.g., 2-fold or more larger than non-hypertrophic cells). It may be accompanied by accumulation of contractile proteins within the individual cardiac cells and activation of embryonic gene expression.

In vitro and in vivo methods for determining the presence of ventricular muscle cell hypertrophy are known. In vitro assays for ventricular muscle cell hypertrophy include those methods described WO00/37095, e.g., increased cell size and increased expression of atrial natriuretic factor (ANP). Changes in cell size are used in a scoring system to determine the extent of hypertrophy. These changes can be viewed with an inverted phase microscope, and the degree of hypertrophy scored with an arbitrary scale of 7 to 0, with 7 being fully hypertrophied cells, and 3 being non-stimulated cells. The 3 and 7 states may be seen in Simpson et al. (1982) Circulation Res. 51: 787-801, FIGS. 2, A and B, respectively. The correlation between hypertrophy score and cell surface area (µm2) has been determined to be linear (correlation coefficient=0.99). In phenylephrine-induced hypertrophy, non-exposed (normal) cells have a hypertrophy score of 3 and a surface area/cell of 581 µm2 and fully hypertrophied cells have a hypertrophy score of 7 and a surface area/cell of 1811 µm2, or approximately 200% of normal. Cells with a hypertrophy score of 4 have a surface area/cell of 771 µm2, or approximately 30% greater size than non-exposed cells; cells with a hypertrophy score of 5 have a surface area/cell of 1109 µm2, or approximately 90% greater size than non-exposed cells; and cells with a hypertrophy score of 6 have a surface area/cell of 1366 µm2, or approximately 135% greater size than non-exposed cells. The presence of ventricular muscle cell hypertrophy preferably includes cells exhibiting an increased size of about 15% (hypertrophy score 3.5) or more. Inducers of hypertrophy vary in their ability to induce a maximal hypertrophic response as scored by the above-described assay. For example, the maximal increase in cell size induced by endothelin is approximately a hypertrophy score of 5.

As used herein, "suppression of cardiac hypertrophy" means a reduction in one of the parameters indicating hypertrophy relative to the hypertrophic condition, or a prevention of an increase in one of the parameters indicating hypertrophy relative to the normal condition. For example, suppression of ventricular muscle cell hypertrophy can be measured as a reduction in cell size relative to the hypertrophic condition. Suppression of ventricular muscle cell hypertrophy means a decrease of cell size of 10% or greater relative to that observed in the hypertrophic condition. More preferably, suppression of hypertrophy means a decrease in cell size of 30% or greater; most preferably, suppression of hypertrophy means a decrease of cell size of 50% or more. Relative to the hypertrophy score assay when phenylephrine is used as the inducing agent, these decreases would correlate with hypertrophy scores of about 6.5 or less, 5.0-5.5, and 4.0-5.0, respectively. When a different agent is used as the inducing agent, suppression is examined relative to the maximum cell size (or hypertrophic score) measured in the presence of that inducer.

Prevention of ventricular muscle cell hypertrophy is determined by preventing an increase in cell size relative to normal cells, in the presence of a concentration of inducer sufficient to fully induce hypertrophy. For example, prevention of hypertrophy means a cell size increase less than 200% greater than non-induced cells in the presence of maximally stimulating concentration of inducer. More preferably, prevention of hypertrophy means a cell size increase less than 135% greater than noninduced cells; and most preferably, prevention of hypertrophy means a cell size increase less than 90% greater than non-induced cells. Relative to the hypertrophy score assay when phenylephrine is used as the inducing agent, prevention of hypertrophy in the presence of a maximally-stimulating concentration of phenylephrine means a hypertrophic score of about 6.0-6.5, 5.0-5.5, and 4.0-4.5, respectively.

In vivo determination of hypertrophy may include measurement of cardiovascular parameters such as blood pressure, heart rate, systemic vascular resistance, contractility, force of heartbeat, concentric or dilated hypertrophy, left ventricular systolic pressure, left ventricular mean pressure, left ventricular end-diastolic pressure, cardiac output, stroke index, histological parameters, and ventricular size and wall thickness. Animal models available for determination of development and suppression of ventricular muscle cell hypertrophy in vivo include the pressure-overload mouse model, RV murine dysfunctional model, transgenic mouse model, and post-myocardial infarction rat model. Medical methods for assessing the presence, development, and suppression of ventricular muscle cell hypertrophy in human patients are known, and include, for example, measurements of diastolic and systolic parameters, estimates of ventricular mass and pulmonary vein flows.

Hypertrophy may be from any cause which is responsive to retinoic acid, including congenital viral, idiopathic, cardiotrophic, or myotrophic causes, or as a result of ischemia or ischemic insults such as myocardial infarction. Typically, the treatment is performed to stop or slow the progression of hypertrophy, especially after heart damage, such as from ischemia, has occurred. Preferably, for treatment of myocardial infarctions, the agent(s) is given immediately after the myocardial infarction, to prevent or lessen hypertrophy.

As used herein, "activity unit" or "1 U" means the quantity of standard product that can induce 50% maximal reaction. In other words, to determine the activity unit for a given active agent, the EC50 must be measured. For example, if the EC50 for a batch of product was 0.067 µg/ml then that would be one unit. Further, if 1 µg of that product is being used then 14.93 U (1/0.067) is being used. The EC50 can be determined by any method known in the art, including the method employed by the inventors in the Examples below. This determination of the activity unit is important for quality control of genetically engineered products and clinically used drugs, permits product from different pharmaceuticals and/or different batch numbers to be quantified with uniform criteria.

In certain embodiments, unit of neuregulin is determined by measuring the activity of neuregulin through kinase receptor activation enzyme-linked immunosorbant assay (KIRA-ELISA) as described in detail in Example 6 below and in WO03/099300, and Sadick et al., 1996, Analytical Biochemistry, 235:207-14, the contents of which are incorporated by reference in their entireties. Briefly, the assay measures neuregulin induced ErbB2 activation and phosphorylation on the adherent breast carcinoma cell line, MCF-7. Membrane proteins are solubilized via Triton X-100 lysis and the receptor is captured in ELISA wells coated with ErbB2-specific antibodies (e.g., H4) with no cross-reaction to ErbB3 or ErbB4. The degree of receptor phosphorylation is then quantified by antiphosphotyrosine ELISA.

B. Neuregulin

The present invention provides methods for treating or preventing heart failure or cardiac hypertrophy in a mammal by extended release of a sustained or varied amount of NRG. Any NRG (e.g., NRG-1, NRG-2, NRG-3 and NRG-4 and isoforms thereof) protein, peptide or fragment can be used in the practice of this invention.

Neuregulin or NRG refers to proteins or peptides that can bind and activate ErbB2, ErbB3, ErbB4 or combinations thereof, including but not limited to all neuregulin isoforms, neuregulin EGF domain alone, polypeptides comprising neuregulin EGF-like domain, neuregulin mutants or derivatives, and any kind of neuregulin-like gene products that also activate the above receptors as described in detail below. In preferred embodiments, neuregulin used in the present invention binds to and activate ErbB2/ErbB4 or ErbB2/ErbB3 heterodimers. Neuregulin used in the present invention can activate the above ErbB receptors and modulate their biological reactions, e.g., stimulate breast cancer cell differentiation and milk protein secretion; induce the differentiation of neural crest cell into Schwann cell; stimulate acetylcholine receptor synthesis in skeletal muscle cell; and/or improve cardiocyte differentiation, survival and DNA synthesis. Assays for measuring the receptor binding activity are known in the art. For example, cells transfected with ErbB-2 and ErbB-4 receptor can be used. After receptor expressing cells are incubated with excess amount of radiolabeled neuregulin, the cells are pelleted and the solution containing unbound radiolabeled neuregulin is removed before unlabeled neuregulin solution is added to compete with radiolabeled neuregulin. EC50 is measured by methods known in the art. EC50 is the concentration of ligands which can compete 50% of bound radiolabeled ligands off the receptor complex. The higher the EC50 value is, the lower the receptor binding affinity is.

Neuregulin used in the present invention includes any neuregulin and isoforms thereof known in the art, including but not limited to all isoforms of neuregulin-1 ("NRG-1"), neuregulin-1 ("NRG-2"), neuregulin-1 ("NRG-3") and neuregulin-4 ("NRG-43"). NRG-1 is described, for example, in U.S. Pat. Nos. 5,530,109, 5,716,930, and 7,037,888; Lemke, Mol. Cell. Neurosci. 1996, 7:247-262; Peles and Yarden, 1993, BioEssays 15:815-824, 1993; Peles et al., 1992, Cell 69, 205-216; Wen et al., 1992, Cell 69, 559-572, 1992, Holmes et al., 1992, Science 256:1205-1210, Falls et al., 1993, Cell 72:801-815, Marchionni et al. 1993, Nature 362:312-8, the contents of which are incorporated by reference in their entireties. NRG-2 is described, for example, in Chang et al., 1997, Nature 387:509-512; Carraway et al., 1997, Nature 387:512-516; Higashiyama et al., 1997, J. Biochem. 122:675-680, Busfield et al., 1997, Mol. Cell. Biol. 17:4007-4014 and International Pat. Pub. No. WO 97/09425), the contents of which are incorporated by reference in their entireties. NRG-3 is described, for example, in Hijazi et al., 1998, Int. J. Oncol. 13:1061-1067, the contents of which are incorporated by reference in their entireties. NRG-4 is described, for example, in Harari et al., 1999 Oncogene. 18:2681-89, the contents of which are incorporated by reference in their entireties.

Neuregulin used in the present invention includes neuregulin mutants or derivatives that comprise one or more amino acid substitutions, deletions, and/or additions that are not present in the naturally occurring neuregulin. Preferably, the number of amino acids substituted, deleted, or added is 1, 2, 3, 4, 5, 6, 7, 8, 9, or 10 amino acids. In one embodiment, such a derivative contains one or more amino acid deletions, substitutions, or additions at the amino and/or carboxy terminal end of the peptide. In another embodiment, such a derivative contains one or more amino acid deletions, substitutions, or additions at any residue within the length of the peptide.

In certain embodiments, the amino acid substitutions may be conservative or non-conservative amino acid substitutions. Conservative amino acid substitutions are made on the basis of similarity in polarity, charge, solubility, hydrophobicity, hydrophilicity, and/or the amphipathic nature of the amino acid residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. In addition, glycine and proline are residues that can influence chain orientation. Non-conservative substitutions will entail exchanging a member of one of these classes for another class.

In certain embodiments, neuregulin used in the present invention is a neuregulin derivative with conservative amino acid substitutions that do not substantially alter their biological activity. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al. Molecular Biology of the Gene, 4th Edition, 1987, The Bejacmin/Cummings Pub. co., p. 224).

In certain embodiments, neuregulin used in the present invention includes neuregulin mutants or derivatives having an amino acid substitution with a non-classical amino acid or chemical amino acid analog. Non-classical amino acids include, but are not limited to, the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general.

Neuregulin used in the present invention includes neuregulin homologue, that is, a polypeptide that exhibits an amino acid sequence homology and/or structural resemblance to neuregulin, or to one of the interacting domains of neuregulin such that it is capable of bind and activate ErbB2/ErbB4 or ErbB2/ErbB3 heterodimers protein kinases. Typically, a protein homologue of a native protein may have an amino acid sequence that is at least 50%, preferably at least 75%, more preferably at least 80%, 85%, 86%, 87%, 88% or 89%, even more preferably at least 90%, 91%, 92%, 93% or 94%, and most preferably 95%, 96%, 97%, 98% or 99% identical to the native protein.

Percent homology in this context means the percentage of amino acid residues in the candidate sequence that are identical (i.e., the amino acid residues at a given position in the alignment are the same residue) or similar (i.e., the amino acid substitution at a given position in the alignment is a conservative substitution, as discussed above), to the corresponding amino acid residue in the peptide after aligning the sequences and introducing gaps, if necessary, to achieve the maximum percent sequence homology. In certain embodiments, neuregulin homologue is characterized by its percent sequence identity or percent sequence similarity with the naturally occurring neuregulin sequence. Sequence homology, including percentages of sequence identity and similarity, are determined using sequence alignment techniques well-known in the art, preferably computer algorithms designed for this purpose, using the default parameters of said computer algorithms or the software packages containing them.

Nonlimiting examples of computer algorithms and software packages incorporating such algorithms include the following. The BLAST family of programs exemplify a preferred, non-limiting example of a mathematical algorithm utilized for the comparison of two sequences (e.g., Karlin & Altschul, 1990, *Proc. Natl. Acad. Sci. USA* 87:2264-2268 (modified as in Karlin & Altschul, 1993, *Proc. Natl. Acad. Sci. USA* 90:5873-5877), Altschul et al., 1990, *J. Mol. Biol.* 215:403-410, (describing NBLAST and)(BLAST), Altschul et al., 1997, *Nucleic Acids Res.* 25:3389-3402 (describing Gapped BLAST, and PSI-Blast). Another preferred example is the algorithm of Myers and Miller (1988 *CABIOS* 4:11-17) which is incorporated into the ALIGN program (version 2.0) and is available as part of the GCG sequence alignment software package. Also preferred is the FASTA program (Pearson W. R. and Lipman D. J., *Proc. Nat. Acad. Sci. USA*, 85:2444-2448, 1988), available as part of the Wisconsin Sequence Analysis Package. Additional examples include BESTFIT, which uses the "local homology" algorithm of Smith and Waterman (Advances in Applied Mathematics, 2:482-489, 1981) to find best single region of similarity between two sequences, and which is preferable where the two sequences being compared are dissimilar in length; and GAP, which aligns two sequences by finding a "maximum similarity" according to the algorithm of Neddleman and Wunsch (*J. Mol. Biol.* 48:443-354, 1970), and is preferable where the two sequences are approximately the same length and an alignment is expected over the entire length.

Examples of homologues may be the ortholog proteins of other species including animals, plants, yeast, bacteria, and the like. Homologues may also be selected by, e.g., mutagenesis in a native protein. For example, homologues may be identified by site-specific mutagenesis in combination with assays for detecting protein-protein interactions. Additional methods, e.g., protein affinity chromatography, affinity blotting, in vitro binding assays, and the like, will be apparent to skilled artisans apprised of the present invention.

For the purpose of comparing two different nucleic acid or polypeptide sequences, one sequence (test sequence) may be described to be a specific "percent identical to" another sequence (reference sequence) in the present disclosure. In this respect, when the length of the test sequence is less than 90% of the length of the reference sequence, the percentage identity is determined by the algorithm of Myers and Miller, *Bull. Math. Biol.*, 51:5-37 (1989) and Myers and Miller, *Comput. Appl. Biosci.*, 4(1):11-17 (1988). Specifically, the identity is determined by the ALIGN program. The default parameters can be used.

Where the length of the test sequence is at least 90% of the length of the reference sequence, the percentage identity is determined by the algorithm of Karlin and Altschul, *Proc. Natl. Acad Sci. USA*, 90:5873-77 (1993), which is incorporated into various BLAST programs. Specifically, the percentage identity is determined by the "BLAST 2 Sequences" tool. See Tatusova and Madden, *FEMS Microbiol. Lett.*, 174(2):247-250 (1999). For pairwise DNA-DNA comparison, the BLASTN 2.1.2 program is used with default parameters (Match: 1; Mismatch: −2; Open gap: 5 penalties; extension gap: 2 penalties; gap x_dropoff: 50; expect: 10; and word size: 11, with filter). For pairwise protein-protein sequence comparison, the BLASTP 2.1.2 program is employed using default parameters (Matrix: BLOSUM62; gap open: 11; gap extension: 1; x_dropoff: 15; expect: 10.0; and wordsize: 3, with filter).

Neuregulin used in the present invention also include neuregulin EGF domain alone, polypeptides comprising neuregulin EGF domain or neuregulin-like gene products that mimic the activities of neuregulin and binds and activates ErbB2, ErbB3, ErbB4 or combinations thereof. As used herein, "epidermal growth factor-like domain" or "EGF-like domain" refers to a polypeptide motif encoded by the neuregulin gene that binds to and activates ErbB2, ErbB3, ErbB4, or combinations thereof, and bears a structural similarity to the EGF receptor-binding domain as disclosed in WO 00/64400, Holmes et al., Science, 256: 1205-1210 (1992); U.S. Pat. Nos. 5,530,109 and 5,716,930; Hijazi et al., Int. J. Oncol., 13:1061-1067 (1998); Chang et al., Nature, 387:509-512 (1997); Carraway et al., Nature, 387:512-516 (1997); Higashiyama et al., J. Biochem., 122: 675-680 (1997); and WO 97/09425, the contents of which are all incorporated herein by reference.

In certain embodiments, neuregulin used in the present invention comprises the EGF-like domain encoded by NRG-1. In some embodiments, EGF-like domain comprises the amino acid sequence of the receptor binding domain of NRG-1. In some embodiments, EGF-like domain comprises the amino acid sequence corresponding to amino acid residues 177-226, 177-237, or 177-240 of NRG-1.

In preferred embodiments, neuregulin used in the present invention comprises the amino acid sequence of:
Ser His Leu Val Lys Cys Ala Glu Lys Glu Lys Thr Phe Cys Val Asn Gly Gly Glu Cys Phe Met Val Lys Asp Leu Ser Asn Pro Ser Arg Tyr Leu Cys Lys Cys Pro Asn Glu Phe Thr Gly Asp Arg Cys Gln Asn Tyr Val Met Ala Ser Phe Tyr Lys Ala Glu Glu Leu Tyr Gln (SEQ ID NO:1), which corresponds to amino acids 177-237 of human NRG-1. The human nucleic acid sequence encoding the fragment is:
agccatcttg taaaatgtgc ggagaaggag aaaactttct gtgtgaatgg aggggagtgc ttcatggtga aagacctttc aaaccccctcg agatacttgt gcaagtgccc aaatgagttt actggtgatc gctgccaaaa ctacgtaatg gcgagcttct acaaggcgga ggagctgtac cag (SEQ ID NO:2).

In certain embodiments, neuregulin used in the present invention comprises the EGF-like domain encoded by NRG-2. In certain embodiments, neuregulin used in the present invention comprises the EGF-like domain encoded by NRG-3. In certain embodiments, neuregulin used in the present invention comprises the EGF-like domain encoded by NRG-4. In certain embodiments, neuregulin used in the present invention comprises the amino acid sequence of Ala Glu Lys Glu Lys Thr Phe Cys Val Asn Gly Gly Glu Cys Phe Met Val Lys Asp Leu Ser Asn Pro (SEQ ID NO:3), as described in U.S. Pat. No. 5,834,229.

C. Extended Release Technology in General

The present invention provides compositions for extended release of neuregulin and methods for preventing, treating or delaying various disease, such as heart failure using such. Extended release of neuregulin allows for simplification of administration scheme, improves clinical efficacy and attenuates adverse events, e.g., related to high blood level of neuregulin. It is contemplated that extended release of neuregulin over a certain period could induce or maintain expression of certain genes for cardiomyocyte growth and/or differentiation, remodeling of muscle cell sarcomeric and cytoskeleton structures, or cell-cell adhesions.

Extended release of neuregulin can be administered by any route according to the judgment of those of skill in the art, including but not limited to orally, inhalationally, parenterally (e.g., intravenously, intramuscularly, subcutaneously, or intradermally). In certain embodiments, neuregulin is administered orally. In certain embodiments, neuregulin is administered intravenously. In certain embodiments, neuregulin is administered intramuscularly. In preferred embodiments, neuregulin is extendedly released to the bloodstream of a mammal.

Neuregulin can be administered by any extended release means or by any delivery devices that are known to those of ordinary skill in the art. Specifically, any extended means or delivery devices for delivering peptides known in the art can be used in the present invention. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, 5,639,480, 5,733,566, 5,739,108, 5,891,474, 5,922,356, 5,972,891, 5,980,945, 5,993,855, 6,045,830, 6,087,324, 6,113,943, 6,197,350, 6,248,363, 6,264,970, 6,267,981, 6,376,461, 6,419,961, 6,589,548, 6,613,358, 6,699,500, 6,740,634, 6,838,076, 6,866,866, 7,087,246, each of which is incorporated herein by reference. Such dosage forms can be used to provide extended release of neuregulin using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. The invention also encompasses single unit dosage forms suitable for oral administration such as, but not limited to, tablets, capsules, gelcaps, and caplets that are adapted for controlled-release.

Extended release of neuregulin provides continuous therapeutic level of neuregulin over a period of time. In some embodiments, neuregulin is released over a period of 1 hour, 2 hours, 4 hours, 6 hours, 8 hours, 10 hours, 12 hours, 14 hours, 16 hours, 20 hours, 24 hours or longer. In some embodiments, neuregulin is released over a period of 1 day, 2 days, 3 days, 4 days, 5 days, 6 days, 7 days, 8 days, 9 days, 10 days or longer. In yet another embodiments, neuregulin is released over a period of 1 week, 2 weeks, 3 weeks, 4 weeks or longer. In another embodiments, neuregulin is released over a period of 1 month, 2 months, 4 months, 8 months, 12 months or longer. In yet another embodiments, neuregulin is released over a period of 1 years, 2 years, 3 years, 4 years or longer. In some embodiments, neuregulin is released over a period of between 1 minutes to 24 hours, 1 hour and 2 week, between 2 hours and 2 week, between 4 hours to 24 hours, between 4 days and 10 days. The amount of time over which neuregulin is released may depend on various factors such as the extended release technology or technologies used.

Extended release of neuregulin maintains neuregulin in the blood within a desirable range, particularly at a level which is at or above the minimum effective therapeutic level and is below the minimum toxic level over a period of time. The serum concentration of neuregulin in patients who received an extended release neuregulin composition can be compared with serum concentrations of patients receiving a non-extended release neuregulin composition (e.g., intravenous administration) at a time when the maximum blood level concentration occurs ($C_{max}$). In a preferred embodiment, the patients receiving an extended release neuregulin composition have a lower maximum serum concentration ($C_{max}$) of neuregulin than the patients receiving a non-extended neuregulin composition. Preferably, the patients receiving an extended release neuregulin composition have a $C_{max}$ less than about 90%, 80%, 70% or 60% of the $C_{max}$ in patients receiving a non-extended release neuregulin composition. More preferably, the patients receiving an extended release neuregulin composition have a $C_{max}$ less than about 50%, 40% or 30% of the $C_{max}$ in patients receiving a non-extended release neuregulin composition. Most preferably, the patients receiving an extended release neuregulin composition have a $C_{max}$ less than about 20%, 10% or less of the $C_{max}$ in patients receiving a non-extended release neuregulin composition. Methods for measuring the concentration of neuregulin in the serum are known in the art. For instance, cells expressing ErbB-2 and ErbB-3 receptors, such as SKBR-3 breast cancer cell line, can be used. 10, 5, 2.5, 1.25, 0.625, 0.312, 0.156, 0.078, 0.039, 0.019 and 0.0079 ng of neuregulin is added to different tubes containing cells separately on ice, then radiolabeled neuregulin (50,000 cpm) is added. The sample solution is mixed and left at 4° C. overnight. Next morning, cells are pelleted and the supernatant is sucked away before the radioactivity is counted. A standard curve is drawn by radioactivity versus unlabeled neuregulin amount. When measuring the concentration of neuregulin in the serum, certain amount of serum is added to tube containing cells on ice, radiolabeled neuregulin (50,000 cpm) is then added, and the sample solution is mixed and left at 4° C. overnight. Next morning, cells are pelleted and the supernatant is sucked away before the radioactivity is counted. The radioactivity is counted and the amount of neuregulin in the serum can be calculated according to the standard curve.

Various extended release profiles can be provided in accordance with the present invention. "Extended release profile" means a release profile in which less than 50% of the total release of neuregulin that occurs over the course of implantation/insertion or other method of administering neuregulin in the body occurs within the first 24 hours of administration. In a preferred embodiment of the present invention, the extended release profile is selected from the group consisting of: (a) the 50% release point occurring at a time that is between 24 and 48 hours after implantation/insertion or other method of administration, (b) the 50% release point occurring at a time that is between 48 and 96 hours after implantation/insertion or other method of administration, (c) the 50% release point occurring at a time that is between 96 and 168 hours (1 week) after implantation/insertion or other method of administration, (d) the 50% release point occurring at a time that is between 1 and 2 weeks after implantation/insertion or other method of administration, (e) the 50% release point occurring at a time that is between 2 and 4 weeks after implantation/insertion or other method of administration, (f) the 50% release point occurring at a time that is between 4 and 8 weeks after implantation/insertion or other method of administration, (g) the 50% release point occurring at a time that is between 8 and 16 weeks after implantation/insertion or other method of administration, (h) the 50% release point occurring at a time that is between 16 and 52 weeks (1 year) after implantation/insertion or other method of administration, and (i) the 50% release point occurring at a time that is between 52 and 104 weeks after implantation/insertion or other method of administration.

Additionally, use of the present invention can reduce the degree of fluctuation ("DFL") of an agent's plasma concentration. DFL is a measurement of how much plasma levels of a drug vary over the course of a dosing interval. The closer the DFL is to zero (0), the less variance there is over the course of a dosing period. Thus a reduced DFL signifies that the difference in peak and trough plasma levels has been reduced. Preferably, the patients receiving an extended release composition have a DFL approximately 90%, 80%, 70% or 60% of the DFL in patients receiving a non-extended release composition. More preferably, the patients receiving an extended release composition have a DFL approximately 50%, 40%, or 30% of the DFL in patients receiving a non-extended release composition. Most preferably, the patients receiving an extended release neuregulin composition have a DFL approximately 20%, 10% or less of the DFL in patients receiving a non-extended release neuregulin composition.

Any technologies known in the art for extended release of a biomolecule can be used in the prevent invention. Generally, the size and frequency of dosing is determined by the pharmacodynamic and pharmacokinetic properties of the active agent. The slower the rate of absorption, the less the blood concentrations fluctuate within a dosing interval. This enables higher doses to be given less frequently. However, many active agents that are readily soluble in the body are usually absorbed rapidly and provide a sudden burst of available drug. An example is hypotension patients taking rapid-release nifedipine products. The use of an extended-release product avoids the high initial blood concentrations which cause the sudden reduction in blood pressure and other significant haemodynamic changes such as reflex tachycardia.

Additionally, some active agents are targeted and removed or destroyed by the body, e.g., immune system, proteases. Drugs with short half-lives for this and other reasons often need to be given the active agent at frequent intervals to maintain blood concentrations within the therapeutic range. There is an inverse correlation between the frequency of dosing and patient compliance. For such agents with relatively short half-lives, the use of extended-release products may maintain therapeutic concentrations over prolonged periods. Thus, a reduction in the number of daily doses offered by extended-release products has the potential to improve compliance. Although specific extended release technologies are disclosed herein, the invention is more general than any specific extended release technology. This includes the discovery that extended release of NRG at low doses unexpectedly improves the function of infarct heart. Further, there are numerous extended release drug delivery technologies currently known in the art. Several are generally discussed below as preferred extended release technologies, but they are offered solely for purposes of illustration and not limitation. Many other related and unrelated technologies are well known in the art and may be employed in the practice of the invention disclosed herein. Additionally, combinations of the extended release technologies discussed herein and/or other extended release technologies known in the art may be employed in the practice of this invention. For example, many companies with specific expertise in extended release drug delivery technologies—e.g., Alza Corp., Durect Corp., Gilead Sciences, Baxter Pharmaceuticals, Brookwood Pharmaceuticals and OctoPlus—offer products and services that can be employed in the practice of this invention. Additionally, a search of patents, published patent applications and related publications will provide those skilled in the art reading this disclosure with significant possible extended release technologies. Thus, one skilled in the art will be able to select the desired extended release technology or technologies for use in the practice of this invention.

C. 1. Osmotic Pumps

In one embodiment of the present invention, the extended release of NRG into the blood comprises the use of an osmotic pump. Osmotic devices have demonstrated utility in delivering beneficial active agents to a target area in a controlled manner over prolonged periods of time. Known devices include tablets, pills, capsules and implantable devices. Tablets and pills can be taken orally, whereas other pumps are implanted subcutaneously or intraperitoneally, or attached to a catheter for intravenous, intracerebral or intraarterial infusion.

Generally, in an osmotic pump system, a core is encased by a semipermeable membrane having at least one orifice. The semipermeable membrane is permeable to water, but impermeable to the active agent. When the system is exposed to body fluids, water penetrates through the semipermeable membrane into the core containing osmotic excipients and the active agent. Osmotic pressure increases within the core and the agent is displaced through the orifice at a controlled, predetermined rate.

In many osmotic pumps, the core contains more than one internal compartment. For example, a first compartment may contain the active agent. A second compartment contains an osmotic agent and/or "driving member." See, e.g., U.S. Pat. No. 5,573,776, the contents of which are incorporated herein by reference. This compartment may have a high osmolality, which causes water to flux into the pump through the semipermeable membrane. The influx of water compresses the first compartment. This can be accomplished, for example, by using a polymer in the second compartment, which swells on contact with the fluid. Accordingly, the agent is displaced at a predetermined rate.

In another embodiments, the osmotic pump may comprise more than one active agent-containing compartment, with each compartment containing the same agent or a different agent. The concentrations of the agent in each compartment, as well as the rate of release, may also be the same or different.

The rate of delivery is generally controlled by the water permeability of the semipermeable membrane. Thus, the delivery profile of the pump is independent of the agent dispensed, and the molecular weight of an agent, or its physical and chemical properties, generally have no bearing on its rate of delivery. Further discussion regarding the principle of operation, the design criteria, and the delivery rate for osmotic pumps is provided in Theeuwes and Yum, Annals of Biomedical Engineering, Vol. 4, No. 4 (1976) and Urquhart et. al., Ann. Rev. Pharmacol. Toxicol. 24:199-236 (1984), the contents of which are incorporated by reference.

Osmotic pumps are well known in the art and readily available to one of ordinary skill in the art from companies experienced in providing osmotic pumps for extended release drug delivery. For example, ALZA's DUROS® technology is an implantable, nonbiodegradable, osmotically driven system that enables delivery of small drugs, peptides, proteins, DNA and other bioactive macromolecules for up to one year; ALZA's OROS® technology embodies tablets that employ osmosis to provide precise, controlled drug delivery for up to 24 hours; Osmotica Pharmaceutical's Osmodex® system includes a tablet, which may have more than one layer of the drug(s) with the same or different release profiles; Shire Laboratories' EnSoTrol® system solubilizes drugs within the core and delivers the solubilized drug through a laser-drilled hole by osmosis; and Alzet® Osmotic pumps are miniature, implantable pumps used for research in mice, rats and other laboratory animals.

A search of patents, published patent applications and related publications will also provide those skilled in the art reading this disclosure with significant possible osmotic pump technologies. For example, U.S. Pat. Nos. 6,890,918; 6,838,093; 6,814,979; 6,713,086; 6,534,090; 6,514,532; 6,361,796; 6,352,721; 6,294,201; 6,284,276; 6,110,498; 5,573,776; 4,200,0984; and 4,088,864, the contents of which are incorporated herein by reference, describe osmotic pumps and methods for their manufacture. One skilled in the art, considering both the disclosure of this invention and the disclosures of these other patents could produce an osmotic pump for the extended release of NRG.

Typical materials for the semipermeable membrane include semipermeable polymers known to the art as osmosis and reverse osmosis membranes, such as cellulose acylate, cellulose diacylate, cellulose triacylate, cellulose acetate, cellulose diacetate, cellulose triacetate, agar acetate, amylase triacetate, beta glucan acetate, acetaldehyde dimethyl acetate, cellulose acetate ethyl carbamate, polyamides, plyurethanes, sulfonated polystyrenes, cellulose acetate ppthalate, cellulose acetate methyl carbamate, cellulose acetate succinate, cellulose acetate dimethyl aminoacetate, cellulose acetate ethyl carbamate, cellulose acetate chloracetate, cellulose dipalmitate, cellulose acetate dioctanoate, cellulose dicaprylate, cellulose dipentanlate, cellulose acetate valerate, cellulose acetate succinate, cellulose propionate, succinate, methyl cellulose, cellulose acetate p-toluene sulfonate, cellulose acetate butyrate, cross-linked selectively semipermeable polymers formed by the coprecipitation of a polyanion and a polycation, semipermeable polymers, lightly cross-linked polystyrene derivatives, cross-linked poly(sodium styrene sulfonate), poly(vinylbenzyltrimethyl ammonium chloride), cellulose acetate having a degree of substitution up to 1 and an acetyl content up to 50%, cellulose diacetate having a degree of substitution of 1 to 2 and an acetyl content of 21 to 35%, cellulose triacetate having a degree of substitution of 2 to 3 and an acetyl content of 35 to 44.8%, as disclosed in U.S. Pat. No. 6,713,086, the contents of which are incorporated herein by reference.

The osmotic agent(s) present in the pump may comprise any osmotically effective compound(s) that exhibit an osmotic pressure gradient across the semipermeable wall against the exterior fluid. Effective agents include, without limitation, magnesium sulfate, calcium sulfate, magnesium chloride, sodium chloride, lithium chloride, potassium sulfate, sodium carbonate, sodium sulfite, lithium sulfate, potassium chloride, sodium sulfate, d-mannitol, urea, sorbitol, inositol, raffinose, sucrose, flucose, hydrophilic polymers such as cellulose polymers, mixtures thereof, and the like, as disclosed in U.S. Pat. No. 6,713,086, the contents of which are incorporated herein by reference.

The "driving member" is typically a hydrophilic polymer which interacts with biological fluids and swells or expands. The polymer exhibits the ability to swell in water and retain a significant portion of the imbibed water within the polymer structure. The polymers swell or expand to a very high degree, usually exhibiting a 2 to 50 fold volume increase. The polymers can be non-crosslinked or crosslinked. Hydrophilic polymers suitable for the present purpose are well known in the art.

The orifice may comprise any means and methods suitable for releasing the active agent from the system. The osmotic pump may include one or more apertures or orifices which have been bored through the semipermeable membrane by mechanical procedures known in the art, including, but not limited to, the use of lasers as disclosed in U.S. Pat. No. 4,088,864. Alternatively, it may be formed by incorporating an erodible element, such as a gelatin plug, in the semipermeable membrane.

Although specific embodiments of osmotic pumps are discussed above, the invention is more general than any specific extended release technology. This includes the discovery that extended release of NRG improves the function of infarct heart and reduces the interior diameter of the left ventricle. There are numerous variations and different types of osmotic pumps currently known in the art and may be employed in the practice of the invention disclosed herein.

C. 2. Poly(ethylene glycol) Coupling

In one embodiment of the present invention, the extended release of NRG into the blood comprises the coupling of the active agent to a polymer, such as Poly(ethylene glycol) (hereinafter referred to as "PEG"). Coupling PEG to biologically active agents has demonstrated utility in delivering active agents to a target area in a controlled manner over prolonged periods of time. Particularly, modification of proteins with PEG has been extensively used within the biotechnology industry to reduce the antigenicity of therapeutically active agents and to extend their in vivo availability. For example, coupling PEG to bovine adenosine deaminase using cyanuric chloride results in a loss of immunogenicity. Similarly, the PEG adduct of both human growth hormone and *E. coli* L-asparaginase has been shown to have an extended circulatory half-life.

Coupling PEG to an active agent or other molecules, e.g., outer surface of liposomes, can improve the efficacy and half-life of the active agent or other molecule, and also reduce its toxicity. Particularly, in an aqueous medium, the PEG molecule is hydrated and in rapid motion. This rapid motion causes the PEG to sweep out a large volume and prevents the approach and interference of other molecules, e.g., immune cells or proteases. Thus, when coupled to PEG, the PEG polymer chains can protect the attached molecule from immune response and other clearance mechanisms, sustaining availability of the active agent.

Generally, polyethylene glycol molecules are connected to the protein via a reactive group found on the protein. Commonly amino groups, such as those on lysine residues or at the N-terminus, are used for attachment. U.S. Pat. Nos. 5,824,784 and 4,002,531 disclose such methods for attaching PEG to an enzyme by reductive alkylation. Lysine residues may be strategically substituted for other amino acids or inserted into a polypeptide sequence to provide additional points of attachment as disclosed in U.S. Pat. No. 4,904,584. Additional methods are known in the art for attaching branched or "multi-armed" PEG-derivatives to proteins as disclosed in U.S. Pat. No. 5,932,462. There are many other methods of attachment known in the art for attaching polymers to cysteine residues, carboxy groups, carbohydrates and other moieties. For example, U.S. Pat. No. 5,900,461 discloses derivatives of PEG and other polymers having one more active sulfone moieties that are highly selective for coupling with thiol moieties instead of amino moieties on molecules.

PEGs can also be used to link macromolecules to a targeting ligand or moiety, which directs the macromolecules to particular areas of interest. U.S. Pat. No. 6,436,386 discloses active agent-polymer conjugates attached to a hydroxyapatite-targeting moiety for delivery of the active agent, such as bone growth factors, to hydroxyapatite surfaces, such as bone.

A wide variety of PEG derivatives are both available and suitable for use in the preparation of PEG-conjugates. For example, NOF Corp.'s SUNBRIGHT® Series provides numerous PEG derivatives, including methoxypolyethylene glycols and activated PEG derivatives, such as methoxy-PEG amines, maleimides and carboxylic acids, for coupling by various methods to drugs, enzymes, phospholipids and other biomaterials and Nektar Therapeutics' Advanced PEGylation also offers diverse PEG-coupling technologies to improve the safety and efficacy of therapeutics.

A search of patents, published patent applications and related publications will also provide those skilled in the art reading this disclosure with significant possible PEG-coupling technologies and PEG-derivatives. For example, U.S. Pat. Nos. 6,436,386; 5,932,462; 5,900,461; 5,824,784; 4,904,584 and 4,002,531, the contents of which are incorporated by reference in their entirety, describe such technologies and derivatives, and methods for their manufacture. Thus, one skilled in the art, considering both the disclosure of this invention and the disclosures of these other patents could couple PEG, a PEG-derivative or some other polymer to NRG for its extended release.

PEG is a well known polymer having the properties of solubility in water and in many organic solvents, lack of toxicity, lack of immunogenecity, and also clear, colorless, odorless and stable. One use of PEG is to covalently attach the polymer to insoluble molecules to make the resulting PEG-molecule conjugate soluble. For these reasons and others, PEG has been selected as the preferred polymer for attachment, but it has been employed solely for purposes of illustration and not limitation. Similar products may be obtained with other water soluble polymers, including without limitation, poly(vinyl alcohol), other poly(alkylene oxides) such as poly(propylene glycol) and the like, poly (oxyethylated polyols) such as poly(oxyethylated glycerol) and the like, carboxymethylcellulose, dextran, polyvinyl alcohol, polyvinyl purrolidone, poly-1,3-dioxolane, poly-1, 3,6-trioxane, ethylene/maleic anhydride, and polyaminoacids. One skilled in the art will be able to select the desired polymer based on the desired dosage, circulation time, resistance to proteolysis, and other considerations.

C. 3. Liposome Packaging

In another embodiment of the present invention, the extended release of NRG into the blood comprises packaging NRG in a liposome, which has demonstrated utility in delivering beneficial active agents in a controlled manner over prolonged periods of time. Liposomes are completely closed bilayer membranes containing an entrapped aqueous volume. Liposomes may be unilamellar vesicles possessing a single membrane bilayer or multilamellar vesicles with multiple membrane bilayers, each separated from the next by an aqueous layer. The structure of the resulting membrane bilayer is such that the hydrophobic (non-polar) tails of the lipid orient toward the center of the bilayer while the hydrophilic (polar) heads orient towards the aqueous phase.

Generally, in a liposome-drug delivery system, the active agent is entrapped in the liposome and then administered to the patient to be treated. However, if the active agent is lipophilic, it may associate with the lipid bilayer.

The immune system may recognize conventional liposomes as foreign bodies and destroy them before significant amounts of the active agent reaches the intended disease site. Thus, in one embodiment, the liposome may be coated with a flexible water soluble polymer that avoids uptake by the organs of the mononuclear phagocyte system, primarily the liver and spleen. Suitable hydrophilic polymers for surrounding the liposomes include, without limitation, PEG, polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxethylacrylate, hydroxymethylcellulose hydroxyethylcellulose, polyethyleneglycol, polyaspartamide and hydrophilic peptide sequences as described in U.S. Pat. Nos. 6,316,024; 6,126,966; 6,056,973; 6,043,094, the contents of which are incorporated by reference in their entirety.

Liposomes may be comprised of any lipid or lipid combination known in the art. For example, the vesicle-forming lipids may be naturally-occurring or synthetic lipids, including phospholipids, such as phosphatidylcholine, phosphatidylethanolamine, phosphatidic acid, phosphatidylserine, phasphatidylglycerol, phosphatidylinositol, and sphingomyelin as disclosed in U.S. Pat. Nos. 6,056,973 and 5,874,104. The vesicle-forming lipids may also be glycolipids, cerebrosides, or cationic lipids, such as 1,2-dioleyloxy-3-(trimethylamino) propane (DOTAP); N-[1-(2,3,-ditetradecyloxy) propyl]-N,N-dimethyl-N-hydroxyethylammonium bromide (DMRIE); N-[1[(2,3,-dioleyloxy)propyl]-N,N-dimethyl-N-hydroxy ethylammonium bromide (DORIE); N-[1-(2,3-dioleyloxy)propyl]-N,N,N-trimethylammonium chloride (DOTMA); 3 [N—(N',N'-dimethylaminoethane) carbamoly] cholesterol (DC-Chol); or dimethyldioctadecylammonium (DDAB) also as disclosed in U.S. Pat. No. 6,056,973. Cholesterol may also be present in the proper range to impart stability to the vesicle as disclosed in U.S. Pat. Nos. 5,916,588 and 5,874,104.

In another embodiment, the liposome is targeted to specific sites within the body of a mammal by the attachment of a targeting ligand or moiety. The targeting ligands are believed to be recognized by receptors or other compounds on the surface of target cells. Typical target ligands include antibodies or antibody fragments, cell-receptor ligands, lectins and the like. For further discussion see U.S. Pat. Nos. 6,316,024 and 6,294,191, the contents of which are incorporated by reference in their entirety.

Such targeting ligands can be attached to liposomes by any means known in the art for the covalent or noncovalent attachment of such ligands to lipsomes. For example, polymer coated liposomes have been modified to achieve site specific delivery of active agents, by attaching a targeting ligand to either the polar head group residues of liposomal lipid components or the free ends of the polymer chains forming the surface coat on the liposomes as described in U.S. Pat. Nos. 6,316,024 and 6,043,094, the contents of which are incorporated by reference in their entirety. Such attachments may be accomplished by, for example, the coupling of proteins to liposomes through the use of a crosslinking agent having at least one maleimido group and an amine reductive function as described in U.S. Pat. No. 5,399,331; linking proteins to liposomes through the use of the glycoprotein streptavidin as described in U.S. Pat. Nos. 4,885,172; 5,059,421 and 5,171,578; the coating of targeted liposomes with polysaccharides; or a vesicle forming lipid may derivatized with a hydrophilic polymer chain, which is end-functionalized for coupling antibodies through the use of a hydrazide or hydrazine group that is reactive toward aldehyde groups as described in U.S. Pat. No. 6,126,966. The end functionalized group may also be 2-pyridyldithiopropionamide, for coupling an antibody or other molecule to the liposome through a disulfide linkage.

The liposomes of this invention can be manufactured by standard techniques known to those of skill in the art. For example, in one embodiment, as disclosed in U.S. Pat. No. 5,916,588, a buffered solution of the active agent is prepared. Then a suitable lipid, such as hydrogenated soy phosphatidylcholine, and cholesterol, both in powdered form, are dissolved in chloroform or the like and dried by rotoevaporation. The lipid film thus formed is resuspended in diethyl ether or the like and placed in a flask, and sonicated in a water bath during addition of the buffered solution of the active agent. Once the ether has evaporated, sonication is discontinued and a stream of nitrogen is applied until residual ether is removed. Other standard manufacturing procedures are described in U.S. Pat. Nos. 6,352,716; 6,294,191; 6,126,966; 6,056,973; 5,965,156; and 5,874,104. The liposomes of this invention can be produced by any method generally accepted in the art for making liposomes, including, without limitation, the methods of the above-cited documents (the contents of which are incorporated herein by reference).

Liposomes are also well known in the art and readily available from companies experienced in providing liposomes for extended release drug delivery. For example, ALZA's (formerly Sequus Pharmaceuticals') STEALTH® liposomal technology for intravenous drug delivery uses a polyethylene glycol coating on liposomes to evade recognition by the immune system; Gilead Sciences (formerly Nexstar's) liposomal technology was incorporated into AmBisome®, and FDA approved treatment for fungal infections; and NOF Corp. offers a wide variety of GMP-grade phospholipids, phospholipids derivatives, and PEG-phospholipids under the tradenames COATSOME® and SUN-BRIGHT®.

A search of patents, published patent applications and related publications will also provide those skilled in the art reading this disclosure with significant possible liposomal technologies. U.S. Pat. Nos. 6,759,057; 6,406,713; 6,352,716; 6,316,024; 6,294,191; 6,126,966; 6,056,973; 6,043,094; 5,965,156; 5,916,588; 5,874,104; 5,215,680; and 4,684,479, the contents of which are incorporated herein by reference, describe liposomes and lipid-coated microbubbles, and methods for their manufacture. Thus, one skilled in the art, considering both the disclosure of this invention and the disclosures of these other patents could produce a liposome for the extended release of NRG.

Although specific embodiments of liposomes are discussed above, the invention is more general than any specific extended release technology. This includes the discovery that extended release of NRG improves the function of infarct heart and reduces the interior diameter of the left ventricle. There are numerous variations and different types of liposomes currently known in the art and may be employed in the practice of the invention disclosed herein.

C. 4. Microsphere Packaging

In another embodiment of the present invention, the extended release of NRG into the blood comprises packaging NRG in a microsphere. Microspheres have demonstrated utility in delivering beneficial active agents to a target area in a controlled manner over prolonged periods of time. Microspheres are generally biodegradable and can be used for subcutaneous, intramuscular and intravenous administration.

Generally, each microsphere is composed of an active agent and polymer molecules. As disclosed in U.S. Pat. No. 6,268,053, the active agent may be centrally located within a membrane formed by the polymer molecules, or, alternatively dispersed throughout the microsphere because the internal structure comprises a matrix of the active agent and a polymer excipient. Typically, the outer surface of the microsphere is permeable to water, which allows aqueous fluids to enter the microsphere, as well as solubilized active agent and polymer to exit the microsphere.

In one embodiment, the polymer membrane comprises crosslinked polymers as disclosed in U.S. Pat. No. 6,395,302. When the pore sizes of the crosslinked polymer are equal or smaller than the hydrodynamic diameter of the active agent, the active agent is essentially released when the polymer is degraded. On the other hand, if the pore size of the crosslinked polymers are larger than the size of the active agent, the active agent is at least partially released by diffusion.

Additional methods for making microsphere membranes are known and used in the art and can be used in the practice of the invention disclosed herein. Typical materials for the outer membrane include the following categories of polymers: (1) carbohydrate-based polymers, such as methylcellulose, carboxymethyl cellulose-based polymers, dextran, polydextrose, chitins, chitosan, and starch (including hetastarch), and derivatives thereof; (2) polyaliphatic alcohols such as polyethylene oxide and derivatives thereof including polyethylene glycol (PEG), PEG-acrylates, polyethyleneimine, polyvinyl acetate, and derivatives thereof; (3) poly(vinyl) polymers such as poly(vinyl) alcohol, poly(vinyl) pyrrolidone, poly(vinyl)phosphate, poly(vinyl)phosphonic acid, and derivatives thereof; (4) polyacrylic acids and derivatives thereof; (5) polyorganic acids, such as polymaleic acid, and derivatives thereof; (6) polyamino acids, such as polylysine, and polyimino acids, such as polyimino tyrosine, and derivatives thereof; (7) co-polymers and block co-polymers, such as poloxamer 407 or Pluronic L-101™ polymer, and derivatives thereof; (8) tert-polymers and derivatives thereof; (9) polyethers, such as poly(tetramethylene ether glycol), and derivatives thereof; (10) naturally occurring polymers, such as zein, chitosan and pullulan, and derivatives thereof; (11) polyimids, such as poly n-tris (hydroxymethyl) methylmethacrylate, and derivatives thereof; (12) surfactants, such as polyoxyethylene sorbitan, and derivatives thereof; (13) polyesters such poly(ethylene glycol) (n)monomethyl ether mono(succinimidyl succinate) ester, and derivatives thereof; (14) branched and cyclopolymers, such as branched PEG and cyclodextrins, and derivatives thereof; and (15) polyaldehydes, such as poly (perfluoropropylene oxide-b-perfluoroformaldehyde), and derivatives thereof as disclosed in U.S. Pat. No. 6,268,053, the contents of which are incorporated herein by reference. Other typical polymers known to those of ordinary skill in the art include poly(lactide-co-glycolide, polylactide homopolymer; polyglycolide homopolymer; polycaprolactone; polyhydroxybutyrate-polyhydroxyvalerate copolymer; poly(lactide-co-caprolactone); polyesteramides; polyorthoesters; poly 13-hydroxybutyric acid; and polyanhydrides as disclosed in U.S. Pat. No. 6,517,859, the contents of which are incorporated herein by reference.

In one embodiment, the microsphere of the present invention are attached to or coated with additional molecules. Such molecules can facilitate targeting, enhance receptor mediation, and provide escape from endocytosis or destruction. Typical molecules include phospholipids, receptors, antibodies, hormones and polysaccharides. Additionally, one or more cleavable molecules may be attached to the outer surface of microspheres to target it to a predetermined site. Then, under appropriate biological conditions, the molecule is cleaved causing release of the microsphere from the target.

The microspheres of this invention are manufactured by standard techniques. For example, in one embodiment, volume exclusion is performed by mixing the active agent in solution with a polymer or mixture of polymers in solution in the presence of an energy source for a sufficient amount of time to form particles as disclosed in U.S. Pat. No. 6,268,053. The pH of the solution is adjusted to a pH near the isoelectric point (pI) of the macromolecule. Next, the solution is exposed to an energy source, such as heat, radiation, or ionization, alone or in combination with sonication, vortexing, mixing or stirring, to form microparticles. The resulting microparticles are then separated from any unincorporated components present in the solution by physical separation methods well known to those skilled in the art and may then be washed. Other standard manufacturing procedures are described in U.S. Pat. Nos. 6,669,961; 6,517,859; 6,458,387; 6,395,302; 6,303,148; 6,268,053; 6,090,925; 6,024,983; 5,942,252; 5,981,719; 5,578,709; 5,554,730; 5,407,609; 4,897,268; and 4,542,025, the contents of which are incorporated by reference in their entirety.

Microspheres are well known and readily available to one of ordinary skill in the art from companies experienced in providing such technologies for extended release drug delivery. For example, Epic Therapeutics, a subsidiary of Baxter Healthcare Corp., developed PROMAXX®, a protein-matrix drug delivery system that produces bioerodible protein microspheres in a totally water-based process; OctoPlus developed OctoDEX®, crosslinked dextran microspheres that release active ingredients based on bulk degradation of matrix rather than based on surface erosion; and Brookwood Pharmaceuticals advertises the availability of its microparticle technologies for drug delivery.

A search of patents, published patent applications and related publications will also provide those skilled in the art reading this disclosure with significant possible microsphere technologies. For example, U.S. Pat. Nos. 6,669,961; 6,517,859; 6,458,387; 6,395,302; 6,303,148; 6,268,053; 6,090,925; 6,024,983; 5,942,252; 5,981,719; 5,578,709; 5,554,730; 5,407,609; 4,897,268; and 4,542,025, the contents of which are incorporated by reference in their entirety, describe microspheres and methods for their manufacture. One skilled in the art, considering both the disclosure of this invention and the disclosures of these other patents could make and use microspheres for the extended release of NRG.

D. Dosage and Frequency of Administration

The amount of neuregulin used in the present invention will vary with the nature and severity of the disease or condition, and the route by which the active ingredient is administered. The frequency and dosage will also vary according to factors specific for each patient depending on the specific therapy (e.g., therapeutic or prophylactic agents) administered, the severity of the disorder, disease, or condition, the route of administration, as well as age, body, weight, response, and the past medical history of the patient. Effective doses may be extrapolated from dose-response curves derived from in vitro or animal model test systems.

Exemplary doses of neuregulin include milligram or microgram amounts of neuregulin per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). For extended release of neuregulin used in the invention, the dosage administered to a patient is typically 0.001 mg/kg to 15 mg/kg of the patient's body weight, based on weight of the active peptide. Preferably, the dosage administered to a patient is between 0.001 mg/kg and 15 mg/kg, 0.005 mg/kg and 10 mg/kg, 0.01 mg/kg and 5 mg/kg, 0.001 mg/kg and 4 mg/kg, 0.005 mg/kg and 3 mg/kg, 0.01 mg/kg and 2 mg/kg, 0.001 mg/kg and 1 mg/kg, 0.005 mg/kg and 0.5 mg/kg, 0.010 mg/kg and 0.2 mg/kg, 0.005 mg/kg and 0.050 mg/kg of the patient's body weight.

Exemplary doses of neuregulin also include unit (U) or unit amounts of neuregulin per kilogram of subject or sample weight (e.g., about 1 U per kilogram to about 5000 U per kilogram, about 10 U micrograms per kilogram to about 1000 per kilogram, or about 100 U per kilogram to about 500 U per kilogram). For extended release of neuregulin used in the invention, the dosage administered to a patient is typically 10 U/kg to 1000 U/kg of the patient's body weight, based on weight of the active peptide. Preferably, the dosage administered to a patient is between 1 U/kg and 10,000 U/kg, 1 U/kg and 5000 U/kg, 10 U/kg and 5000 U/kg, 10 U/kg and 1000 U/kg, 50 U/kg and 2000 U/kg, 50 U/kg and 1000/kg, 50 U/kg and 500 U/kg, 100 U/kg and 1000 U/kg, 100 U/kg and 500 U/kg, 100 U/kg and 200 U/kg, of the patient's body weight.

In general, the recommended daily dose range of neuregulin in the methods of the invention for the conditions described herein lie within the range of from about 0.001 mg to about 1000 mg per day. Specifically, a total daily dose range should be between 0.001 mg per day and 15 mg per day, 0.005 mg per day and 10 mg per day, 0.01 mg per day and 5 mg per day, 0.001 mg per day and 4 mg per day, 0.005 mg per day and 3 mg per day, 0.01 mg per day and 2 mg per day, 0.001 mg per day and 1 mg per day, 0.005 mg per day and 0.5 mg per day, 0.010 mg per day and 0.2 mg per day. In managing the patient, the therapy can be initiated at a lower dose, perhaps about 0.1 µg to about 1 µg and increased if necessary up to about 20 µm mg to about 1000 µg per day as either a single dose or divided doses, depending on the patient's global response. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with individual patient response. In certain embodiments, neuregulin is administered in an amount of about 1 U/day to about 10,000 U/day. In some embodiments, it is administered in an amount of about 1 U/day to about 5000 U/day. In some embodiments, it is administered in an amount of about 10 U/day to about 2000 U/day. In some embodiments, it is administered in an amount of about 10 U/day to about 1000 U/day. In some embodiments, it is administered in an amount of about 100 U/day to about 200 U/day.

Neuregulin can also be administered in a dosing schedule or "therapeutic cycle." Daily dosage of neuregulin in the therapeutic cycle is described in detail above. The therapeutic cycle can last 2 days, 5 days, 7 days, 10 days, two weeks, three weeks, four weeks, five weeks, or six weeks.

In certain embodiments, neuregulin is administered daily for each day of the therapeutic cycle. In certain embodiments, neuregulin is administered consecutively for three, four, five, six, seven, eight, nine, ten, eleven or twelve days in a therapeutic cycle.

In certain embodiments, in a therapeutic cycle neuregulin is administered on day 1 of the cycle and the cycle concludes with one or more days of no neuregulin administration In some embodiments, neuregulin is administered daily for 3, 5, 7, or 10 days followed by a resting period in a therapeutic cycle.

E. Combinational Therapy

In one embodiment, the present invention is useful in preventing heart failure and cardiomyopathy in patients being treated with a drug that causes cardiac hypertrophy or heart failure, e.g., fludrocortisone acetate or herceptin. NRG may be administered prior to, simultaneously with, or subsequent to a drug which causes such cardiac diseases.

In another embodiment of the invention, NRG is administered in combination with an effective amount of a compound that acts to suppress a different hypertrophy induction pathway than NRG. In an alternative embodiment, NRG is administered with such hypertrophy suppressors and/or additional components, without limitation, a cardiotrophic inhibitor such as a Ct-1 (cardiotrophin-1) antagonist, an ACE inhibitor, such as captopril (Capoten®), and/or human growth hormone and/or IGF-I (Insulin like growth factor I) in the case of congestive heart failure, or with another anti-hypertrophic, myocardiotrophic factor, anti-arrhythmic, or inotropic factor in the case of other types of heart failure or cardiac disorder.

In another embodiment of the invention, NRG is administered in combination with current therapeutic approaches for treatment of heart failure, including, without limitation, ACE inhibitors and other vasodilators, diuretics, digitalis preparations, beta blockers, blood thinners, angiotensin II receptor blockers, calcium channel blockers or potassium.

ACE inhibitors, which prevent the conversion of angiotensin I to angiotensin II, are vasodilators that cause the blood vessels to expand, lowering the blood pressure and reducing the heart's workload. Vasodilators suitable for use in embodiments of the present invention include, without limitation, the following drugs: quinapril (Accupril®), ramipril (Altace®), captopril (Capoten®), benazepril (Lotensin®), fosinopril (Monopril®), lisinopril (Prinivil® or Zestril®), enalapril (Vasotec®), moexipril (Univasc®), trandolapril, and perindopril. Additional vasodilators useful in the present invention, include, without limitation, isosorbide dinitrate (Isordil®), nesiritide (Natrecor®), hydralazine (Apresoline®), nitrates and minoxidil.

Diuretics cause the kidneys to remove sodium and water from the blood stream, reducing the heart's workload, and include, without limitation, the following drugs: hydrochlorothiazide (HydroDIURIL®), chlorothiazide (Diuril®), furosemide (Lasix®), bumetanide (Bumex®), spironolactone (Aldactone®), triamterene (Dyrenium®), metolazone (Zaroxolyn®), torsemide, indapamide, polythiazide, amiloride, and combination agents (Dyazide®).

Digitalis preparations increase the force of the heart's contractions and include, without limitation, digoxin (Lanoxin®) and digitoxin.

Beta blockers reduce the heart's tendency to beat faster and include, without limitation, the following drugs: carvedilol (Coreg®) metoprolol (Lopressor® or Toprol XL®, atenolol, bisoprolol, labetalol, propranolol, sotalol, pindolol, penbutolol, acebutolol, timolol, nadolol, and betaxolol.

Blood thinners for use in embodiments of the present invention, include, without limitation, warfarin (Coumadin®) and heparin.

Embodiments of the present invention may also use angiotensin II receptor blockers, which, rather than lowering the levels of angiotensin II (as ACE inhibitors do), prevents angiotensin II from effecting the heart and blood vessels. Angiotensin II receptor blockers suitable for use in the present invention, include, without limitation, iosartan (Cozaar®), valsartan (Diovan®), irbesartan (Avapro®), candesartan, eprosartan, telmisartan, and olmesartan.

Calcium channel blockers are generally used to treat high blood pressure often associated with heart failure. Calcium channel blockers suitable for use in the present invention include, without limitation, amlodipine (Norvasc®).

In alternative embodiments of the present invention, extended release of NRG can also be combined with the administration of drug therapies for the treatment of heart diseases such as hypertension. For example, NRG can be administered with endothelin receptor antagonists, such as antibodies to the endothelin receptor, and peptides or other such small molecule antagonists; 3-adrenoreceptor antagonists such as carvedilol; x,-adrenoreceptor antagonists; antioxidants; compounds having multiple activities (e.g., 3-blocker/a-blocker/anti-oxidant); carvedilol-like compounds or combinations of compounds providing multiple functions found in carvedilol; growth hormone, etc.

Neuregulin agonists alone or in combination with other hypertrophy suppressor pathway agonists or with molecules that antagonize known hypertrophy induction pathways, are useful as drugs for in vivo treatment of mammals experiencing heart failure, so as to prevent or lessen heart failure effects.

Therapeutic formulations of agonist(s) for treating heart disorders are prepared for storage by mixing the agonist(s)

having the desired degree of purity with optional physiologically acceptable carriers, excipients, or stabilizers (Remington's Pharmaceutical Sciences, 16th edition, Oslo, A., Ed., 1980), in the form of lyophilized cake or aqueous solutions. Acceptable carriers, excipients, or stabilizers are non-toxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobins; hydrophilic polymers such as olyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counter ions such as sodium; and/or non-ionic surfactants such as Tween, Pluronics, or polyethylene glycol (PEG). The antagonist(s) are also suitably linked to one of a variety of nonproteinaceous polymers, e.g., polyethylene glycol, polypropylene glycol, or polyalkylenes, in the manner set forth in U.S. Pat. Nos. 4,640,835; 4,496,689; 4,301,144; 4,670,417; 4,791,192 or 4,179,337. The amount of carrier used in a formulation may range from about 1 to 99%, preferably from about 80 to 99%, optimally between 90 and 99% by weight.

The agonist(s) to be used for in vivo administration should be sterile. This is readily accomplished by methods known in the art, for example, by filtration through sterile filtration membranes, prior to or following lyophilization and reconstitution. The agonist(s) ordinarily will be stored in lyophilized form or in solution.

Therapeutic agonist compositions generally are placed into a container having a sterile access port, for example, an intravenous solution bag or vial having a stopper pierceable by a hypodermic injection needle. The agonist(s) administration is in a chronic fashion only, for example, one of the following routes: injection or infusion by intravenous, intraperitoneal, intracerebral, intramuscular, intraocular, intraarterial, or intralesional routes, orally or using sustained-release systems as noted above.

As discussed above, suitable examples of sustained-release preparations include semipermeable matrices of solid hydrophobic polymers containing the protein, which matrices are in form of shaped articles, e.g., films, or microcapsules. Examples of sustained-release matrices include polyesters, hydrogels (e.g., poly(2-hydroxyethyl-methacrylate) as described by Langer et al. (1981) J. Biomed. Mater. Res. 15: 167-277 and Langer (1982) Chem. Tech. 12: 98-105, or poly(vinyl alcohol)), polylactides (U.S. Pat. No. 3,773,919, EP 58,481), copolymers of L-glutamic acid and gamma ethyl-L-. glutamate (Sidman et al. (1983) Biopolymers 22: 547-556), non-degradable ethylene-vinyl acetate (Langer et al. (1981) supra) degradable lactic acidglycolic acid copolymers such as the Lupron Depot™ (injectable microspheres composed of lactic acid-glycolic acid copolymer and leuprolide acetate), and poly-D-(−)-3-hydroxybutyric acid (EP 133,988).

The agonist(s) also may be entrapped in microcapsules prepared, for example, by coacervation techniques or by interfacial polymerization (for example, hydroxymethylcellulose or gelatin-microcapsules and poly[methylmethacylate] microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, supra.

While polymers such as ethylene-vinyl acetate and lactic acid-glycolic acid enable release of molecules for over 100 days, certain hydrogels release molecules for shorter time periods. When encapsulated molecules remain in the body for a long time, they may denature or aggregate as a result of exposure to moisture at 37° C., resulting in a loss of biological activity and possible changes in immunogenicity. Rational strategies can be devised for stabilization depending on the mechanism involved, e.g., using appropriate additives, and developing specific polymer matrix compositions.

Sustained-release agonist(s) compositions also include liposomally entrapped agonists(s). Liposomes containing agonists(s) are prepared by methods known in the art, for example, those disclosed in DE 3,218,121; Epstein et al. (1985) Proc. Natl. Acad. Sci. USA 82: 3688-3692; Hwang et al. (1980) Proc. Natl. Acad. Sci. USA 77:4030-4034: EP 52,322; EP 36,676; EP 88,046; EP 143,949; EP 142,641; Japanese patent application 83-118008; U.S. Pat. Nos. 4,485,045 and 4,544,545; and EP 102, 324. A specific example of suitable sustained-release formulation is in EP 647,449.

In another embodiment of the present invention, NRG is combined with or administered in concert with other agents for treating congestive heart failure, including ACE inhibitors (as discussed above), CT-1 inhibitors, human growth hormone, and/or IGF-I. The effective amounts of such agents, if employed will be at the clinician's discretion. Dosage administration and adjustment are determined by methods known to those skilled in the art to achieve the best management of congestive heart failure and ideally takes into account use of diuretics or digitalis, and conditions such as hypotension and renal impairment. The dose will additionally depend on such factors as the type of drug used and the specific patient being treated. Typically the amount employed will be the same dose as that used if the drug were to be administered without agonist; however, lower doses may be employed depending on such factors as the presence of side-effects the condition being treated, the type of patient, and the type of agonists and drug, provided the total amount of agents provides an effective dose for the condition being treated.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

F. Kits

The invention also provides kits for carrying out the therapeutic regiments of the invention. Such kits comprise in one or more containers therapeutically effective amounts of NRG described herein, alone or in combination with other agents, in pharmaceutically acceptable form and in combination with an extended release technology as described herein. Instructions are optionally included for administration of the extended release NRG composition by a physician or by the patient.

G. EXAMPLES

As shown in the Examples, the invention resides in the discovery that extended release of NRG activates the AKT or ERK signaling pathway as effectively as NRG delivered by other methods, and improves the function of infarct heart much more than NRG delivered by other methods. However, the invention also has broader application to other diseases and disorders given that NRG's interactions with ErbB receptors have been implicated in other diseases and disorders, e.g., diseases of the central and peripheral nervous system. Examples of other diseases and disorders, include, various cardiovascular diseases, cancer, neural system disease and/or muscle diseases, including muscular dystrophy (e.g., Duchenne, Limb-girdle) and multiple sclerosis, spinal injury, eye and ear diseases, diabetes, schizophrenia, and Alzheimer's.

The invention will be further illustrated by reference to the following non-limiting Examples. The examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used but some experimental errors and deviations should be accounted for.

Example 1

Phosphorylation of AKT and ERK in the Left Ventricle of Normal Rats after NRG is Infused by Different Methods.

To compare the effect of NRG with various treating methods on the signal transduction inside the cardiac myocytes in the left ventricle, we infused NRG by intravenous (hereinafter referred to as "IV"), intramuscular (hereinafter referred to as "IM") and IV glucose tolerance test (hereinafter referred to as "IVGTT").

Wistar male rats (Shanghai Animal Center of Chinese Academy of Science), which weighed 180±20 grams, were numbered, weighed, and divided into groups. Each group contained three rats. One group received IV injection of 4 ml/kg (volume/body weight) of vehicle (10 mM $Na_2HPO_4$—$NaH_2PO_4$, 150 mM NaCl, 0.2% human serum albumin (HSA), 5% mannitol, pH 6.0) as a control. Four other groups of rats received IM injection of 4 ml/kg (volume/body weight) of NRG (37.3 U/ml recombinant human NRG fragment (from the 177th to 237th amino acid sequence of human NRG1β2 produced by Zensun Science & Technology—batch number 200503002)) dissolved in vehicle (as described above). Another four groups of rats received IV injection of 4 ml/kg (volume/body weight) of NRG (as described above). Another five groups of rats received 20 μl/min of glucose tolerance test infusion of NRG (as described above) by IV injection (IVGTT) for two hours. Thus, the total amount of NRG administered to each rat (except for the vehicle group) was 149.3 U/kg of body weight.

Rats were killed separately at 20 min, 1 hr, 2 hr, 4 hr and 6 hr. The left ventricles of each group of rats were cut into pieces in cold lysis buffer (50 mM Tris pH 7.4, 5 mM EDTA, 150 mM NaCl, 1% Triton X-100, 2 mM $Na_3VO_4$, 50 mM NaF, 2 mM PMSF, protease inhibitor cocktail (no EDTA, Roche)) after pooled, and washed with cold PBS. The ventricles were then homogenized in ice water and centrifuged (Kendro Biofuge) at 12,000 rpm for 5 min at 4° C. in 1.5 ml Eppendorf tubes. The supernatant was collected and spun one more time, then stored at −80° C. The samples were thawed and spun again before use. The protein concentration of each sample was determined by BCA protein assay (Pierce BCA protein assay kit). A certain amount of each sample was mixed with 2× sample buffer (0.125M Tris ph 6.8, 20% glycerol, 4% SDS, 0.2M DTT, 0.012% bromophenol blue) and boiled for electrophoresis before transfer to PVDF membrane (Millipore). The phosphorylation of AKT and ERK, as well as the amount of AKT and ERK in each sample was detected with antibodies (ERK antibody and phosphorylated ERK antibody (Santa Cruz Biotechnology); AKT antibody and phosphorylated AKT antibody (Cell Signaling)).

The time course of phosphorylation of AKT and ERK in the left ventricle of normal rats when NRG was infused by each of these different methods is shown in FIG. 1. Compared to the vehicle, NRG infused by IM, IV and IVGTT all activated sustained phosphorylation of ERK. AKT phosphorylation induced by each method peaked at 20 min and decreased at 1 hr, but increased again at 2 hr, where it maintained a high level from 4 hr to 6 hr. Thus, there is no obvious difference among the different methods of injecting NRG with respect to their ability to sustain phosphorylation of ERK and AKT. This indicates that NRG infused constantly is as effective as injection of NRG. Thus, IVGTT infusion is a potential method for treating poor cardiac conditions.

Example 2

The Function of Left Ventricle Coronary Artery Ligated Rat Heart after Neuregulin Treatment by Different Methods As osmotic pump is a way to deliver NRG constantly (as IVGTT), we examined whether NRG infused by osmotic pump was as effective as conventional IV injection in restoring the function of myocardial infarct (MI) heart.

A. Rat Left Ventricle Coronary Artery Ligation and Echocardiography

Wistar male rats (Shanghai Animal Center of Chinese Academy of Science), which weighed 200±20 g, were anesthetized by intraperitoneally injecting 100 mg/kg (drug/body weight) of ketamine. The neck and chest were depilated and sanitized. An incision was made in the middle front neck to expose the tracheae. An 18G catheter overneedle was inserted into the tracheae between the 3rd and 5th cartilage of tracheae. After the needle was drawn out, a plastic cannula was pushed into the trachea 1-2 cm and fixed to connect the Rodent Ventilator (SAR-830/P ventilator—Inspiratory flow rate, 1 ml/100 g/breath; Respiratory rate, 60 breaths/min). Another incision was made on the left front chest. The skin was blunt dissected to expose the fourth and fifth rib, then the fourth rib was cut by elbowed mosquito forceps. The ventilator (as described above) was linked to the cannula and turned on, and the heart was exposed to check the status of lung and heart. The pericardium was rived off to identify the left atria and the pulmonary arterious cone after the heart was exteriorized through the incision. The left ventricle anterior descending coronary artery between them was ligated tight with 6/0 medical suture before the heart was replaced into the thorax. The thoracic wall was stitched. The ventilator was blocked to full fill the lung. The chest muscle and skin was stitched after the air in the thoracic cavity was gently squeezed out. The ventilators were removed from the rats until constant spontaneous respiration resumed.

The cardiac function of the rats was then examined by echocardiography (Philips Sonos 7500 S4 probe) on the 14th day after ligation. The rats with ejection fraction (hereinafter "EF") values from 30 to 50 percent were separated and grouped (15 rats per group).

B. Treating the Ligated Rats with Neuregulin.

The rats were weighed on the 15th day after left ventricle coronary ligation to determine the amount of NRG needed.

Rats in the vehicle group received 0.4 ml/100 g (volume/body weight) of vehicle by IV injection. The vehicle was injected once a day for five days, stopped for two days, and then injected for another five days.

The IM and IV groups of rats received IM and IV injection of NRG, respectively (the amount of NRG was 149.3 U/kg (protein/body weight), the volume was 0.4 ml/100 g). The NRG was injected once a day for five days, stopped for two days, and then injected for another five days.

As discussed further below, the IVGTT group had osmotic pumps (ALZET osmotic pump 2ML1) implanted on the fifth day after grouping. Each pump contained 2 ml of NRG solution, which contained 933.1 U of NRG (as a rat now weighed about 250 g) and the infusion speed was about 18.7 U/kg/h. Thus, the maximum drug concentration compared to about 2.67 U/kg by IV injection.

After 7 days, cardiac function of all rats was checked again by echocardiography (Philips Sonos 7500 S4 probe). The next day, hemodynamic parameter check and anatomy check were also undertaken to further confirm the cardiac function of the rats.

B. 1. Transplantation of Osmotic Pump into Rats (all Steps Must be Sterile)

1 ml of sterile water and 1 ml of sterile 0.9% saline was injected into a vial of NRG (993.1 U, 62.5 µg) in the hood successively. The NRG solution was drawn into a sterile syringe. A blunt-tipped needle was exchanged for the PE60 tube to fix the tube. The distal end of the vein surrounding the PE60 tube was tied tight to further fix the tube. Using a hemostat, a tunnel was formed by blunt separation of the skin from the incision to scapula. A pocket was finally made on the back of the rat in the midscapular region by spreading the skin further. The pump was slid through the tunnel into the pocket with the flow moderator pointing away from the incision. The skin incision was then closed with a suture. The rats were put back into the animal room after revival and were fed as usual.

C. Experimental Results

The function of MI heart following NRG infusion by IVGTT and IV is shown in Table 1 below. In Table 1 "IVS", "LVEDD", "PW", "LVESD", "EF", "FS" and "CC" stand for interventricular septum, left ventricle end diastolic dimension, posterior wall thickness, left ventricle end systolic dimension, ejection fraction, fractional shortening and cardiac cycle, respectively. Here EF and FS reflect the contractility of heart, especially for left ventricle.

EF=(end diastolic volume-end systolic volume)/end diastolic volume

FS=(end diastolic dimension-end systolic dimension)/end diastolic dimension

In Table 1, P<0.01 for LVEDD, LVESD, EF and FS in IVGTT or IV group compared with their counterparts in the vehicle group, indicating highly significant difference.

TABLE 1 cardiac function of MI rats after NRG infusion by IVGTT and IV

| | IVS cm | LVEDD cm | PW cm | LVESD cm | EF % | FS % | CC ms |
|---|---|---|---|---|---|---|---|
| Vehicle | 0.168 ± 0.005 | 0.952 ± 0.082 | 0.173 ± 0.009 | 0.819 ± 0.107 | 34.3 ± 5.0 | 14.5 ± 2.4 | 162.5 ± 23.1 |
| IVGTT | 0.169 ± 0.007 | 0.857 ± 0.093 | 0.190 ± 0.013 | 0.644 ± 0.061 | 54.6 ± 5.4 | 25.2 ± 3.0 | 173.1 ± 22.5 |
| IV | 0.177 ± 0.027 | 0.912 ± 0.081 | 0.189 ± 0.013 | 0.759 ± 0.099 | 40.5 ± 8.9 | 17.5 ± 4.6 | 164.5 ± 18.2 | syringe and the bubble in the syringe was removed. The pump was held upright and the needle was inserted through the small opening at the top of the upright pump until it could go no further. The plunger was pushed slowly to add NRG solution into the pump until the solution began to overflow the pump. The needle was removed and the pump was wiped clean. The transparent cap of the flow moderator was taken off to expose a short stainless steel tube. The steel tube was then inserted into one end of a 5 cm PE60 tube. The syringe needle was inserted into another end of the PE60 tube. The plunger of syringe was pushed to add NRG solution to the flow moderator until it was full. The long tube of the flow moderator was then inserted into the pump until its white flange attached to the pump. The needle was drawn out of the flow moderator before soaking the pump in sterile 0.9% saline at 37° C. overnight.

The rats were anesthetized by Ketamine (as described above). The area between neck and shoulder of the rats was depilated and sanitized. The body was covered with a piece of sterile wet cloth. An incision was then carefully made in the skin between the scapulae to locate and separate the external jugular vein. The distal end of the vein from the heart was ligated. A small hole was made by eye scissors on the wall of the external jugular vein and enlarged by microforceps. The PE60 tube connected to the osmotic pump was inserted 2 cm into the vein through the hole. The proximal end of the vein from the heart was then bound with NRG infused by osmotic pump dramatically increased the cardiac function of MI rats compared to the IV group. Particularly, the EF value—a measurement of the heart's blood pumping efficiency that can be used to estimate the function of the left ventricle—in the IVGTT group was 59.18% higher than that of the vehicle group, and 34.81% higher than the IV group. Additionally, the FS value—also a way of measuring left ventricle performance—of the IVGTT group was 73.79% higher than that of the vehicle group, and 44.0% higher than the IV group. These results show that extended release of NRG is more effective than conventional IV injection for improving cardiac function.

Surprisingly, NRG infused by osmotic pump not only greatly increased the cardiac function of MI rats compare with the IV group, but also reduced the interior diameter of the left ventricle. Specifically, the average Left Ventricle End Diastolic Dimension (hereinafter referred to as "LVEDD") of the IVGTT group was 9.98% smaller than that of the vehicle group, and 6.03% smaller than the IV group. Additionally, the Left Ventricle End Systolic Dimension (hereinafter referred to as "LVESD") of the IVGTT group was 21.37% smaller than that of the vehicle group, and 15.15% smaller than the IV group. These results show that administering NRG constantly can reduce left ventricular volume and mass, thereby improving left ventricular health and performance.

Example 3

Heart Function of Myocardial Infarcted Rats after Neuregulin was Constantly Intravenously Infused by Syringe Pump (Zhejiang University Medical Instrument Co. LTD, WZS 50-F2)

In this example, syringe pump is used for extended release of neuregulin in human patients. Syringe pump can pump the solution continuously at certain speed into the bloodstream through a needle injected into the vein in rat tail. For syringe pump, it's easy to control the infusion time and speed. Neuregulin was intravenously infused by syringe pump at different speed for different time per day into MI rats to better time period and speed for treatment.

Grouped MI rats was treated by intravenous injection of 4 ml/kg (volume/body weight) vehicle everyday for 10 days (group A); or intravenous injection of 10 µg/kg neuregulin (2.5 µg/ml) everyday for 10 days (group B); or intravenous syringe pump infusion of neuregulin (0.625 µg/ml) at 1.25 µg/kg/h with 4 hours per day for 10 days (group C); or intravenous syringe pump infusion of neuregulin (1.25 µg/ml) at 2.5 µg/kg/h with 4 hours per day for 10 days (group D); or intravenous syringe pump infusion of neuregulin (0.625 µg/ml) at 0.625 µg/kg/h with 8 hours per day for 10 days (group E); or intravenous syringe pump infusion of neuregulin (1.25 µg/ml) at 1.25 µg/kg/h with 8 hours per day for 10 days (group F). Echocardiography was then performed for all groups to examine the function of heart.

FS value by around 45.49%. Surprisingly, although MI rats in group E received only half amount of neuregulin for group F, the EF or FS value is nearly the same. The results showed that after neuregulin was continuously intravenously infused by syringe pump for 8 or more hours per day it could enhance the cardiac function.

Example 4

The Cardiac Function of MI Rats after Extended Hypodermic Infusion of NRG by Osmotic Pump Left ventricle coronary artery ligation and transplantation of osmotic pump into rats was performed in the same way as in example 2, except the amount of NRG injected into the pump was 1791.3 U (125 µg), and the pump was embedded without a tube connected to the vein to make NRG infusion hypodermic. The infusion speed is 37.33 U/kg/h.

IV infusion was started at the same time as extended hypodermic infusion so the IV group was treated with NRG for 7 days. The amount of NRG for the IV group was also changed to 223.95 U/kg.

The function of MI heart following NRG infusion by extended hypodermic and IV is shown in Table 3. In Table 3, $P<0.01$ for LVEDD, LVESD, EF and FS in the IVGTT and the IV group compared with their counterparts in the vehicle group, indicating a highly significant difference.

TABLE 2 echocardiography data for MI rats after intravenous syringe pump infusion (ISPI) or IV injection of NRG

| | | IVS cm | LVEDD cm | PW cm | LVESD cm | EF % | FS % | HR/ min |
|---|---|---|---|---|---|---|---|---|
| A | vehicle | 0.057 ± 0.003 | 0.947 ± 0.041 | 0.142 ± 0.013 | 0.811 ± 0.047 | 34.5 ± 3.3 | 14.4 ± 1.6 | 418 ± 51 |
| B | IV | 0.060 ± 0.005 | 0.924 ± 0.060 | 0.164 ± 0.016 | 0.770 ± 0.057 | 41.5 ± 2.6 | 17.8 ± 1.6 | 382 ± 52 |
| C | ISPI 1.25 µg/kg/h 4 h/day | 0.059 ± 0.005 | 0.935 ± 0.050 | 0.156 ± 0.013 | 0.779 ± 0.067 | 41.2 ± 5.7 | 17.7 ± 2.8 | 395 ± 30 |
| D | ISPI 2.5 µg/kg/h 4 h/day | 0.061 ± 0.004 | 0.943 ± 0.058 | 0.160 ± 0.015 | 0.762 ± 0.055 | 43.7 ± 5.4 | 19.0 ± 2.9 | 391 ± 41 |
| E | ISPI 0.625 µg/kg/h 8 h/day | 0.062 ± 0.006 | 0.941 ± 0.061 | 0.164 ± 0.011 | 0.742 ± 0.079 | 47.4 ± 8.6 | 21.1 ± 4.5 | 391 ± 48 |
| F | ISPI 1.25 µg/kg/h 8 h/day | 0.061 ± 0.004 | 0.966 ± 0.038 | 0.166 ± 0.019 | 0.766 ± 0.045 | 47.2 ± 4.2 | 20.8 ± 2.5 | 364 ± 33 |

$P<0.01$ for LVEDD, LVESD, EF and FS in any of ISPI or IV group compared with their counterparts in the vehicle group, indicating highly significant difference. HR means heart rate.

As shown in table 2, compared with the vehicle group, neuregulin by IV (B group) enhanced the EF value of MI rats by 20.29%, intravenous syringe pump infusion for 4 h/day (C, D group) was just as effective as IV, while neuregulin by intravenous syringe pump infusion for 8 h/day (E, F group) enhanced the EF value by around 37.10%. At the same time, compared with the vehicle group, neuregulin by IV injection (B group) enhanced the FS value of MI rats by 23.61%, intravenous syringe pump infusion for 4 h/day (C, D group) was as effective as IV, while neuregulin by intravenous syringe pump infusion for 8 h/day (E, F group) enhanced the

TABLE 3 cardiac function of MI rats after extended hypodermic (EHI) and IV infusion of NRG

| | IVS cm | LVEDD cm | PW cm | LVESD cm | EF % | FS % | CC ms |
|---|---|---|---|---|---|---|---|
| Vehicle | 0.174 ± 0.005 | 1.02 ± 0.077 | 0.185 ± 0.012 | 0.876 ± 0.098 | 33.9 ± 7.9 | 14.3 ± 3.8 | 153 ± 19 |
| EHI | 0.177 ± 0.006 | 0.908 ± 0.079 | 0.209 ± 0.023 | 0.712 ± 0.091 | 48.4 ± 9.3 | 21.7 ± 5.1 | 153 ± 11 |
| IV | 0.171 ± 0.007 | 1.013 ± 0.111 | 0.188 ± 0.010 | 0.874 ± 0.124 | 33.9 ± 6.8 | 14.3 ± 3.3 | 157 ± 15 |

Table 3 shows that extended hypodermic infusion of NRG significantly increased the cardiac function of MI rats compared to the IV and vehicle groups. Compared to vehicle group, extended hypodermic infusion of NRG enhanced the EF value of MI hearts 42.77%, the FS value 51.75%. As discussed above, the EF and FS values are ways of measuring the heart's blood pumping efficiency and can be used to estimate the function of the left ventricle. Thus, these results show that extended release of NRG is much more effective than conventional IV injection for improving cardiac function.

Extended hypodermic infusion of NRG also reduced interior diameter of the left ventricle. Specifically, the LVEDD of MI hearts decreased 10.98% and the LVESD decreased 18.72% compare to vehicle group. IV injection of NRG in this experiment did not have an obvious effect on the cardiac function of MI heart compare to vehicle. The results show that extended hypodermic infusion of NRG can reduce left ventricular volume and mass, thereby improving left ventricular health and performance, which suggests that it may also be used as a treatment for heart failure.

Example 5

Heart Function of Myocardial Infarcted Rats after Neuregulin was Constantly Hypodermically Infused by Syringe Pump Neuregulin was further infused by syringe pump at different speed for different time per day into MI rats.

Grouped MI rats was treated by intravenous injection of 4 ml/kg (volume/body weight) vehicle everyday for 10 days (group A); or intravenous injection of 10 µg/kg neuregulin (2.5 µg/ml) everyday for 10 days (group B); or hypodermic injection (HI) of 10 µg/kg neuregulin (2.5 µg/ml) everyday for 10 days (group C); hypodermic syringe pump infusion of neuregulin (1.25 µg/ml) at 2.5 µg/kg/h with 4 hours per day for 10 days (group D); or hypodermic syringe pump infusion of neuregulin (1.11 µg/ml) at 1.67 µg/kg/h with 6 hours per day for 10 days (group E); or hypodermic syringe pump infusion of neuregulin (1.25 µg/ml) at 1.25 µg/kg/h with 8 hours per day for 10 days (group F). Echocardiography was then performed for all groups to examine the function of heart.

lin by hypodermic syringe pump infusion for 4 h/day (D group) enhanced the EF value by 12.47%, neuregulin by hypodermic syringe pump infusion for 6 h/day (E group) made the EF value jump to 22.90%, neuregulin by hypodermic syringe pump infusion for 8 h/day (E group) also raised the EF value by 20.10%. At the same time, compared with the vehicle group, neuregulin by IV (B group) enhanced the FS value of MI rats by 11.24%, neuregulin by hypodermic injection (C group) enhanced the FS value of MI rats by 7.10%, while neuregulin by hypodermic syringe pump infusion for 4 h/day (D group) enhanced the FS value by 14.20%, neuregulin by hypodermic syringe pump infusion for 6 h/day (E group) made the FS value jump to 26.63%, neuregulin by hypodermic syringe pump infusion for 8 h/day (E group) also raised the FS value by 26.04%. The results showed that after neuregulin was continuously hypodermically infused by syringe pump for 6 or more hours per day could it increased the cardiac function dramatically.

Example 6

PEG Coupling of NRG and Activity of PEG Coupled NRG

A, PEG Coupling and Isolation of PEG Coupled NRG

PEG (mPEG-SPA-5000, NEKTAR) was added into 10 ml 20 mM PBS (pH 8.0) containing 1 mg/ml NRG (PEG:NRG=1:1, molar ratio) and mixed quickly, and the mixture was gently stirred at room temperature for 30 min, then certain amount of glacial acetic acid was added to stop coupling reaction. The mixture was then loaded onto a gel filtration column (S100, Pharmacia) to separate the components. Each peak fraction was collected and its sample was prepared for SDS-PAGE. After electrophoresis, the gel was stained by $BaI_2$ and Coomassie brilliant blue sequentially to detect PEG and NRG separately.

Figure 2:
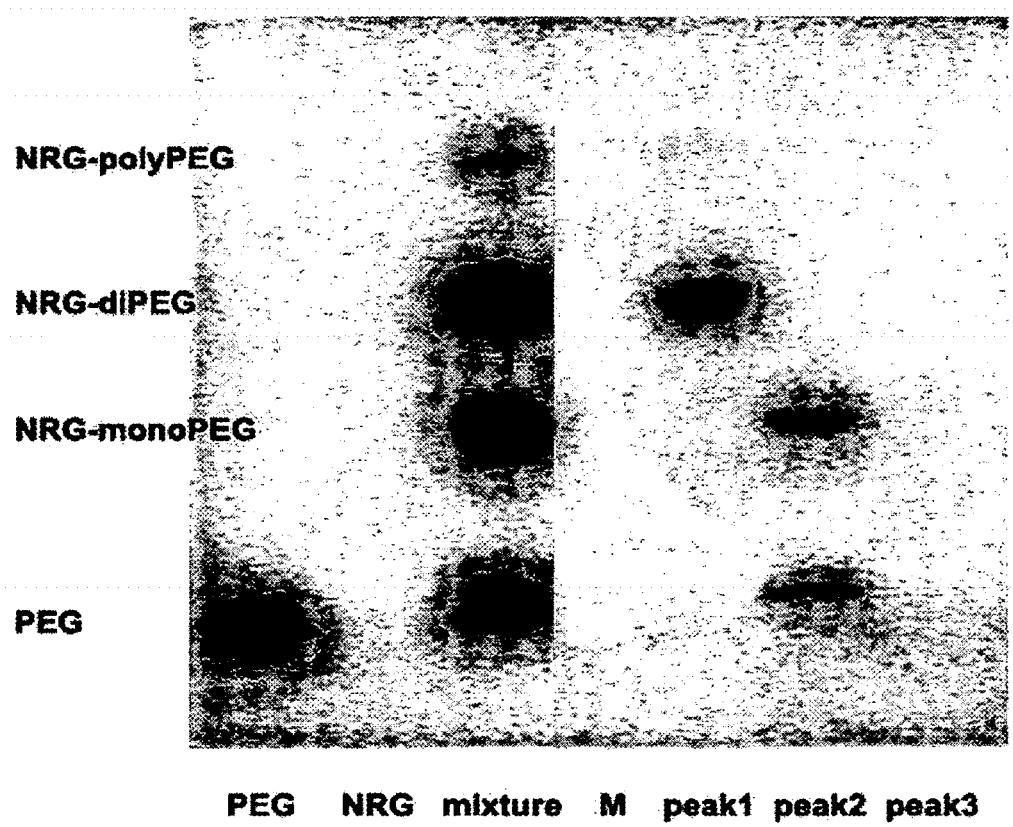
FIG. 2 shows gel stained by $BaI_2$ to detect PEG. In the figure, "mixture" means the solution of PEG and NRG mixture after their reaction. "M", "peak1", "peak2" and "peak3" stand for protein marker and elution peak fraction 1, 2 and 3 of the mixture from the S100 column. "NRG-mono-PEG", "NRG-di-PEG" and "NRG-poly-PEG" mean NRG coupled to one PEG, two PEG and multiple (at least 3) PEG, respectively.

As shown in FIG. 2 for $BaI_2$ stained gel, the mixture contains PEG monomer, NRG-monoPEG, NRG-diPEG and NRG-polyPEG. After the mixture was loaded onto a S100 gel filtration column, the components were well separated into NRG-polyPEG and NRG-diPEG (peak1), NRG-monoPEG and PEG (peak2).

TABLE 4 echocardiography data for MI rats after hypodermic syringe pump infusion (HSPI) or IV injection of NRG

| | | IVS cm | LVEDD cm | PW cm | LVESD cm | EF % | FS % | HR/ min |
|---|---|---|---|---|---|---|---|---|
| A | vehicle | 0.060 ± 0.007 | 0.906 ± 0.107 | 0.151 ± 0.027 | 0.757 ± 0.130 | 39.3 ± 10.8 | 16.9 ± 6.1 | 388 ± 33 |
| B | IV | 0.063 ± 0.004 | 0.812 ± 0.045 | 0.159 ± 0.010 | 0.726 ± 0.047 | 43.4 ± 2.8 | 18.8 ± 1.4 | 385 ± 33 |
| C | HI | 0.063 ± 0.003 | 0.909 ± 0.054 | 0.163 ± 0.011 | 0.744 ± 0.048 | 42.1 ± 3.7 | 18.1 ± 1.9 | 390 ± 40 |
| D | HSPI 2.5 µg/kg/h 4 h/day | 0.065 ± 0.007 | 0.933 ± 0.055 | 0.160 ± 0.016 | 0.754 ± 0.069 | 44.2 ± 6.5 | 19.3 ± 3.4 | 385 ± 32 |
| E | HSPI 1.67 µg/kg/h 6 h/day | 0.067 ± 0.003 | 0.880 ± 0.073 | 0.168 ± 0.019 | 0.693 ± 0.076 | 48.3 ± 6.0 | 21.4 ± 3.5 | 404 ± 38 |
| F | HSPI 1.25 µg/kg/h 8 h/day | 0.066 ± 0.005 | 0.899 ± 0.056 | 0.168 ± 0.014 | 0.709 ± 0.098 | 47.2 ± 11.8 | 21.3 ± 8.2 | 377 ± 44 |

P<0.01 for LVEDD, LVESD, EF and FS in any of HSPI, HI or IV group compared with their counterparts in the vehicle group, indicating highly significant difference. HR means heart rate.

Figure 3:
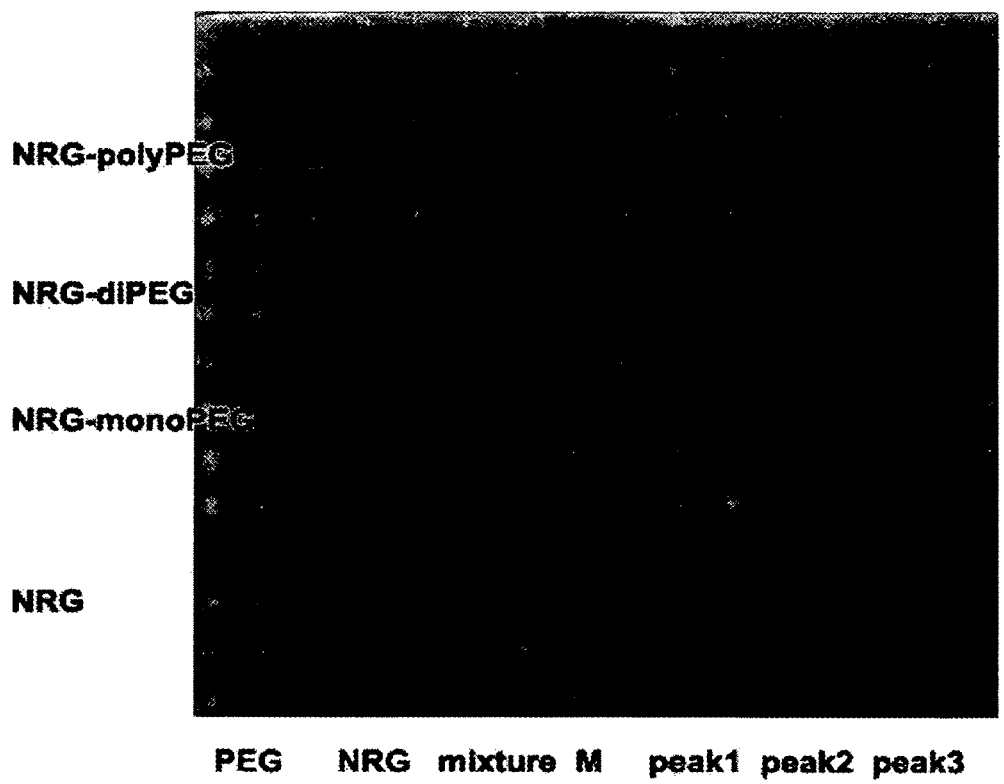
FIG. 3 shows gel coomassie stained to detect NRG protein. The abbreviations are the same as in FIG. 2. In the M lane, the molecular weight for each band (from bottom to above) is 14.4 kD, 20.1 kD, 31.0 kD, 43.0 kD, 66.2 kD and 97.4 kD respectively.

As shown in table 4, compared with the vehicle group, neuregulin by IV (B group) enhanced the EF value of MI rats by 10.43%, neuregulin by hypodermic injection (C group) enhanced the EF value of MI rats by 7.12%, while neuregu- Coomassie stained gel in FIG. 3 further confirmed that peak1 and peak2 contain NRG which was coupled to PEG, while peak3 contains only NRG.

B, Measuring Activity of PEG Coupled NRG

MCF-7 cells was harvested, counted, pelleted and resuspended into DMEM (with 10% serum and 9 µg/ml insulin) at $5×10^4$ cells/ml. 100 µl cell suspension was added to each well of 96 well plate and the plate was incubated at 37° C.

overnight. The cells were then washed 3 times with PBS and grew in serum free DMEM for another 24 hours.

ErbB2 antibody H4 (Zensun, anti-ErbB2 monoclonal antibody) was diluted to 6 µg/ml by coating buffer (50 mM $Na_2CO_3$—$NaHCO_3$, pH9.6), and added to 96 well plate 50 µl/well. The plate was left at 4° C. overnight to coat with antibody.

DMEM was sucked away from the starved MCF-7 cells, and 100 µl serial dilutions of NRG, NRG-monoPEG or NRG-diPEG in DMEM was added to each well separately. DMEM was added to two wells as blank. The plate was incubated at 37° C. for 20 min. The cells were washed once with PBS before adding 100 µl/well lysis buffer (50 mM Hepes, pH 8.0, 150 mM NaCl, 2 mM sodium orthovanadate, 0.01% thimerosal, 1% Triton X-100 and one protease inhibitor cocktail tablet per 25 ml solution) and lysing at 4° C. for 30 min. The plate was then shaken gently to completely lyse and remove cells from the plate and centrifugated at 15000 rpm for 15 min.

The plate with coating antibody was washed five times with washing buffer (10 mM PBS, pH7.4, 0.05% Tween 20) before adding 200 µl/well of 5% nonfat milk in washing buffer. The plate was incubated at 37° C. for 2 hours before washed again 3 times with washing buffer.

A 90 µl solution of lysed cells was drawn from each well in culture plate and transferred to corresponding well in coated plate. Following incubation at 37° C. for 1 hour, the coated plate with cell lysis was washed again 5 times with washing buffer and treated with 100 µl suitable concentration of horseradish peroxidase (HRP) conjugated anti-phosphotyrosine monoclonal antibody (Santa Cruz Biotechnology) at 37° C. for 1 hour. After the plate was washed again 5 times with washing buffer, 100 µl freshly prepared HRP substrate solution [50 mM citric acid, 100 mM $Na_2PO_4$, pH 5.0, 0.2 mg/ml 3,3',5,5'-tetramethylbenzidine (TMB), 0.003% $H_2O_2$] was added to each well before the plate was incubated at 37° C. for 10 min. Finally 50 µl of 2N $H_2SO_4$ was added to each well to destroy HRP activity. The OD value at 450 nm for each well was read on a microplate reader (BIO-RAD Model 550), and EC50 was the concentration of NRG which achieved 50% of maximum OD value. The lower the EC50, the higher the activity.

The EC50 of NRG, NRG-monoPEG and NRG-diPEG was shown in Table 5.

TABLE 5

EC50 of NRG, NRG-monoPEG and NRG-diPEG

| sample | EC50 µg/ml |
|---|---|
| NRG | 0.070 |
| NRG-monoPEG | 0.070 |
| NRG-diPEG | 0.098 |

From table 5, we can see clearly that EC50 of NRG-monoPEG is the same as that of NRG, while EC50 of NRG-diPEG is 40% higher. This means that NRG-monoPEG has the same activity as NRG in vitro, but the activity of NRG-diPEG is 40% lower.

Example 7

Extended Release of Neuregulin Reduces Side Effects of Neuregulin Administration This examples shows that compared with long time or high dose administration, extended release of neuregulin can reduce side effects, such as gastrointestinal disorder or pericardial effusion, associated with neuregulin administration.

NRG-1β was administered intravenously by syringe pump to two groups of monkeys, each consisting of twenty four healthy rhesus monkeys (twelve male and twelve female, weighing about 5-7 kg). Group I was infused with NRG-1β for twelve hours a day for fourteen days, at the speed of 1 ug/kg/hr. No Side effect was observed in this group. Group II was infused for twenty four hours a day for fourteen days, at the speed of 1 ug/kg/hr. In Group II, about 3-5 ml pericardial effusion in the heart of monkeys was observed.

Two groups of healthy individuals were administered the same amount of NRG-1β per day for 10 days. Eight individuals in Group I, were infused with NRG-1β for four hours each day for ten days at speed of 0.3 µg/kg/hr. In this group, each individual on average experienced gastrointestinal disorder about two times during the ten-day period. Six individuals were infused with NRG-1β for two hours each day for ten days at speed of 0.6 µg/kg/hr. In Group II, each individual on average experienced gastrointestinal disorder about five times during the ten-day period.

These results show that extended release of neuregulin can reduce adverse side effects associated with long time or high dose neuregulin administration. These results suggest that intravenously or hypodermically infusion for short time or lower dosage per day could reduce the side effects of 24-hour neuregulin infusion.

Example 8

Gene Expression by Extended Released NRG in the Left Ventricle of Myocardial Infarcted Rat In this example, myocardial infarcted rats were infused with NRG-1β and gene expression pattern in the left ventricle of these rats was analyzed by microarray. Compare with myocardial infarcted rats infused with vehicle, rats infused with NRG have different gene expression pattern. After extended release of NRG, thymosin beta like protein mRNA level increased 3.10 times; defensin beta 1 mRNA level increased 2.87 times; growth associated protein mRNA level increased 2.16 times; mRNA level of thymosin beta 4, Laminin gamma 1, myocardin, PI3K gamma regulatory subunit almost all doubled, while mRNA level of Elastin and PI3K gamma was nearly the same as before. It shows that neuregulin changes the expression level of various proteins in heart.

The scope of the invention is not limited by the description of the examples. Modifications and alterations of the present invention will be apparent to those skilled in the art without departing from the scope and spirit of the present invention. Therefore, it will be appreciated that the scope of this invention is to be defined by the appended claims, rather than by the specific examples which have been presented by way of example.

What is claimed is:

1. A method for ameliorating or delaying a heart disease in a mammal comprising
   (i) releasing a therapeutically effective amount of neuregulin comprising the amino acid sequence of SEQ ID NO: 1, wherein the neuregulin is released to the mammal over a period of 8 hours or longer per day using a syringe pump, wherein the heart disease is selected from the group consisting of heart failure, cardiac hypertrophy and myocardial infarction in a mammal, wherein the neuregulin is released intravenously at a rate of about 0.625 µg/kg/h, and
   (ii) increasing ejection fraction value or fractional shortening value in the mammal,
   thereby ameliorating or delaying the heart disease in the mammal.

2. The method of claim 1, wherein the amino acid sequence of the neuregulin consists of SEQ ID NO:1.

3. The method of claim 1, wherein the neuregulin is attached to a polymer.

4. The method of claim 3, wherein the polymer is poly(ethylene glycol) or a poly(ethylene glycol) derivative.

5. The method of claim 1, wherein the neuregulin is attached to a liposome or microsphere.

6. The method of claim 1, wherein the mammal is human.

7. A method for ameliorating or delaying a heart disease in a mammal comprising
   (i) releasing a therapeutically effective amount of neuregulin comprising the amino acid sequence of SEQ ID NO: 1, wherein the neuregulin is released to the mammal over a period of 4 hours or longer per day using an osmotic pump, wherein the heart disease is selected from the group consisting of heart failure, cardiac hypertrophy and myocardial infarction in a mammal, wherein the neuregulin is released at a rate of about 18.7 U/kg/h, and
   (ii) decreasing left ventricle end diastolic dimension (LVEDD) or left ventricle end systolic dimension (LVESD) in the mammal,
   thereby ameliorating or delaying the heart disease in the mammal.

8. The method of claim 7, wherein the amino acid sequence of the neuregulin consists of SEQ ID NO:1.

9. The method of claim 7, wherein the neuregulin is attached to a polymer.

10. The method of claim 7, wherein the neuregulin is attached to a liposome or microsphere.

* * * * *

SEQUENCE LISTING

<160> NUMBER OF SEQ ID NOS: 3

<210> SEQ ID NO 1
<211> LENGTH: 61
<212> TYPE: PRT
<213> ORGANISM: Homo sapiens

<400> SEQUENCE: 1

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Lys Ala Glu Glu Leu Tyr Gln
    50                  55                  60

<210> SEQ ID NO 2
<211> LENGTH: 183
<212> TYPE: DNA
<213> ORGANISM: Homo sapiens

<400> SEQUENCE: 2
agccatcttg taaaatgtgc ggagaaggag aaaactttct gtgtgaatgg aggggagtgc        60
ttcatggtga aagaccttc aaaccctcg agatacttgt gcaagtgccc aaatgagttt       120
actggtgatc gctgccaaaa ctacgtaatg gcgagcttct acaaggcgga ggagctgtac       180
cag                                                                    183

<210> SEQ ID NO 3
<211> LENGTH: 23
<212> TYPE: PRT
<213> ORGANISM: Homo sapiens

<400> SEQUENCE: 3

Ala Glu Lys Glu Lys Thr Phe Cys Val Asn Gly Gly Glu Cys Phe Met
1               5                   10                  15

Val Lys Asp Leu Ser Asn Pro
            20